(12) United States Patent
Stoll et al.

(10) Patent No.: US 6,267,717 B1
(45) Date of Patent: Jul. 31, 2001

(54) APPARATUS AND METHOD FOR TREATING A BODY STRUCTURE WITH RADIATION

(75) Inventors: Hans-Peter Stoll, Indianapolis; Keith L. March; Gary Hutchins, both of Carmel, all of IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/052,073

(22) Filed: Mar. 31, 1998

(51) Int. Cl.[7] ....................................................... A61N 5/00
(52) U.S. Cl. ....................................................... 600/4; 600/1
(58) Field of Search ............................................... 600/1–8

(56) References Cited

U.S. PATENT DOCUMENTS

| | | |
|---|---|---|
| 4,241,728 | 12/1980 | Mirell . |
| 4,364,376 | 12/1982 | Bigham . |
| 4,883,459 | 11/1989 | Calderon . |
| 5,616,114 | 4/1997 | Thornton et al. . |

OTHER PUBLICATIONS

Bertrand et al., "Intravascular radiation therapy in atherosclerotic promises and premises", European Heart Journal (1997) 18, 1385–1395.

Amols et al., "Dosimetry of a radioactive coronary balloon dilation catheter for treatment of neaointimal hyperplasia", Med. Phys 23 (10), Oct. 1996, 1783–1788.

*Primary Examiner*—John P. Lacyk
(74) *Attorney, Agent, or Firm*—Dann, Dorfman, Herrell, Herrell, P.C.

(57) ABSTRACT

An apparatus for treating a body structure with radiation and a method for using the same. The apparatus comprising a concentrator for receiving a solution comprising a radioactive material and for increasing the concentration of the radioactive material in solution; a calibrator operatively associated with the concentrator for measuring a level of radiation associated with the radioactive material; and a delivery unit for transferring the solution directly from the apparatus to a balloon catheter.

100 Claims, 14 Drawing Sheets

APPARATUS AND METHOD FOR TREATING A BODY STRUCTURE WITH RADIATION

FIELD OF THE INVENTION

The present invention relates to an apparatus and method for treating a body structure with radiation and, in particular, an apparatus and method for treating a body structure with a radioactive material having a short half-life.

BACKGROUND OF THE INVENTION

As an alternative to vascular surgery, balloon angioplasty has become a common method for unblocking narrowed or occluded blood vessels. In this procedure, an angioplasty balloon is inflated within a stenosed vessel in order to dilate the vessel to provide an enlarged lumen. Although balloon angioplasty has been successful in restoring flow in stenotic or occluded vessels, these vessels often restenose due to excessive neointima formation, inward vessel remodeling, and elastic recoil of the diseased tissue. It has been determined that restenosis after coronary balloon angioplasty requires additional treatment in about 35–40% of treated lesions. Although various pharmacological, mechanical, and radiological methods have been utilized, the rate of restenosis has continued to be unacceptably high.

Recently, it was shown in a porcine model that post angioplasty irradiation of the vessel effectively reduced the restenotic response following an experimentally induced coronary overstretch lesion. The attention to date has been focused on gamma ray (e.g., $^{192}$Ir and $^{125}$I) and beta particle (e.g., $^{32}$p, $^{89}$Sr-$^{90}$Y, and $^{131}$I) emitting radioisotopes. The relatively long half-lives of those species mean that the species can be conveniently produced off-site and then transported to the particular institution where the treatment is to occur.

One approach for treating a vessel with radiation to prevent restenosis has been to use radioactive materials in solid form, such as radioactive seeds, coils, or wires. The radioactive materials are enclosed by a catheter and, accordingly, do not come in contact with the patient's blood, thereby eliminating the risk of inadvertently releasing the radioactive material into the patient's blood stream. When gamma ray and beta particle emitters are used, the radiotoxicity associated with direct contact between the radioactive material and the patient's blood stream stems from the very long physical half-lives of these species, as well as from the fact that these emitters tend to accumulate in critical organs like the bone marrow. Further, the use of radioactive materials in solid, as opposed to liquid, form minimizes the shut-down period required to adequately decontaminate a laboratory in the event that the radioactive material escapes from the catheter. However, the radiation source in the proposed devices is difficult to center within the body structure being treated. Accurate centering of the radiation source is required to insure equal dosing along the length and circumference of the body structure being treated. Accordingly, such devices suffer from the disadvantage of over dosing some sections of the body structure being treated and under dosing other sections.

A second approach has been to use a radiation source in liquid form wherein the liquid is contained within an angioplasty balloon positioned within the body structure being treated. However, a rupture of the balloon would release the radioactive liquid directly into the patient's blood stream. Since balloon failure is believed to occur in about 0.1% of cases, special precautions must be taken to minimize the risk of whole-body exposure in the event of a balloon rupture. Towards that end, the use of balloon catheters with multiple wall layers has been proposed. In these devices, a second wall layer would contain the radioisotope in case one layer ruptured. However, these devices have a complicated structure, are expensive to manufacture, and have thicker front profiles making them more difficult to handle.

In light of the foregoing, it would be highly advantageous to provide a system and method for treating a body structure with radiation wherein the system and method minimize the risk of whole-body exposure to radiation under all circumstances for both the patient and the staff. Towards that end, the system and method preferably utilizes a radioactive material having a relatively short half-life (e.g., less than about 2 days). Preferably, the system should comprise means for cheaply and conveniently producing the radiation as close to the time of use as is practical. In addition, the system should be able to provide a therapeutic dose of radiation uniformly along the entire length and circumference of the body structure being treated in a reasonable amount of time (e.g., about 2–5 minutes). Further, the system should provide means for safely and easily handling the radioactive material, dosing the patient, and disposing of the radioactive material.

SUMMARY OF THE INVENTION

The present invention relates to an apparatus for treating a body structure with radiation. The apparatus serves four primary functions. First, the apparatus enables a user to transport a liquid radioactive material directly from a radioisotope generator to a treatment device, such as a balloon catheter. Accordingly, use of the apparatus minimizes the extent to which the radioactive material must be handled, the potential for error, and the likelihood of contamination. Second, the apparatus minimizes the user's risk of exposure to radiation. Third, the apparatus can be used to insure that the correct dose of radiation is applied to the body structure. And fourth, the apparatus can be used to concentrate the radioactive material in a solution having a volume which matches the volume of the balloon being used.

In one embodiment, the apparatus in accordance with the present invention comprises a concentrator for receiving a first solution comprising the radioactive material and for producing a second, more concentrated radioactive solution comprising the radioactive material. The concentrator functions to insure that the volume of the second solution is less than the volume of the first solution. Accordingly, the volume of the second solution can be adjusted to match the volume of the balloon used to treat the body structure.

In one particular embodiment, the concentrator comprises a cartridge having a first open end, a second open end, and a hollow cavity formed between the first and second open ends. The cartridge is provided with a first inlet for introducing the first solution into the cavity through the first open end of the cartridge. Towards that end, the concentrator can be operatively connected with a radioisotope generator which produces the first solution. The generator may be a parent-daughter radioisotope generator, such as those available for the production of $^{68}$Ga or $^{188}$Re. Alternatively, the generator may be a cyclotron for the production of $^{11}$C, $^{13}$N, $^{18}$F, or $^{15}$O. By connecting the concentrator to the generator, the solution can be transferred from the generator to the concentrator with a minimal risk of leakage.

A separating medium may be contained within the cavity of the cartridge within the concentrator. The separating medium comprises a material, such as an ion-exchange resin, which selectively bonds to the radioactive material and not the solute in which the radioactive material is dissolved. The apparatus further comprises a syringe for flushing the separating medium with an elution fluid.

The apparatus may also comprise a calibrator, operatively associated with the concentrator, for measuring a level of radiation associated with the radioactive material. For example, the calibrator may comprise means for directly measuring the level of radiation, such as a Geiger-Muller counter, or means for indirectly measuring the level of radiation, such as a scintillation counter.

In addition, the apparatus comprises a delivery unit for connecting the apparatus to a dosing device having a balloon, such as a balloon catheter and guide wire assembly. The delivery unit comprises a fluid conduit having a first inlet operatively connected to the concentrator for receiving the second, more concentrated solution from the concentrator. In addition, a second inlet is provided for connecting a pressure syringe to the fluid conduit. A pressure gauge may be operatively connected between the fluid conduit and the pressure syringe for measuring the pressure within the pressure syringe. Further, the fluid conduit comprises an outlet so that the second solution can be transferred from the concentrator to the balloon. In operation, the pressure syringe functions to expel the second, more concentrated solution through the outlet of the delivery unit and into the balloon. A three-way valve or stopcock is provided on the fluid conduit to enable the outlet to be connected to either the first or the second inlet, or to be isolated from both the first and second inlets.

In another embodiment, the apparatus in accordance with the present invention comprises a syringe for receiving a solution comprising a radioactive material from a generator and a delivery unit, operatively connected to the syringe, for transferring the solution from the syringe to a balloon. The apparatus may further comprise a calibrator, operatively associated with the syringe, for measuring a level of radiation associated with the radioactive material. The calibrator may comprise means for directly measuring the level of radiation, such as a Geiger-Müller counter. Alternatively, the calibrator may comprise means for indirectly measuring the level of radiation, such as a scintillation counter.

In still another embodiment, the apparatus in accordance with the present invention comprises a syringe for receiving a solution comprising a radioactive material. The syringe comprises a plunger and a pressure meter positioned near a forward end of the plunger for measuring the pressure of fluid contained within the syringe. A locking mechanism is provided such that the plunger is freely slidable within the syringe when the locking mechanism is in an unlocked position and the plunger is restrained by the locking mechanism when the locking mechanism is in a locked position. The locking mechanism comprises a central bore having internal threads. The internal threads along the central bore of the locking mechanism engage external threads along the plunger thereby enabling the plunger to be longitudinally moved within the syringe by rotation of the plunger. The syringe may further comprise a sleeve of scintillating material positioned about the syringe for measuring a level of radiation associated with the radioactive material.

The present invention also relates to a method for treating a body structure with a radioactive material. The method comprises a transfer step wherein a solution comprising a radioactive material is directly transferred from a generator to a dosing apparatus. Once the radioactive material is contained within the dosing apparatus, an optional concentration step may be performed. The concentration step is used to insure that substantially all of the radioactive material is contained in a solution having a volume which is about the same as the volume of a balloon which is to be used to contain the radioactive material adjacent to the body structure being treated. The concentration step may reduce the volume of the solution through evaporation. Alternatively, the radioactive material may be removed from the first solution and dissolved in a second solution, the volume of the second solution being less than the volume of the first solution. A level of radiation associated with the radioactive material is then measured, in order to be able to determine an exposure time which will result in a desired dose of radiation being delivered to the body structure. The desired exposure time can be determined based on the level of radiation measured and the size and volume of the balloon being used. Once the exposure time has been determined, the balloon is positioned adjacent to the body structure at a position along the body structure which is to be treated with radiation. The solution is then transferred to the balloon and maintained within the balloon for the exposure time.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
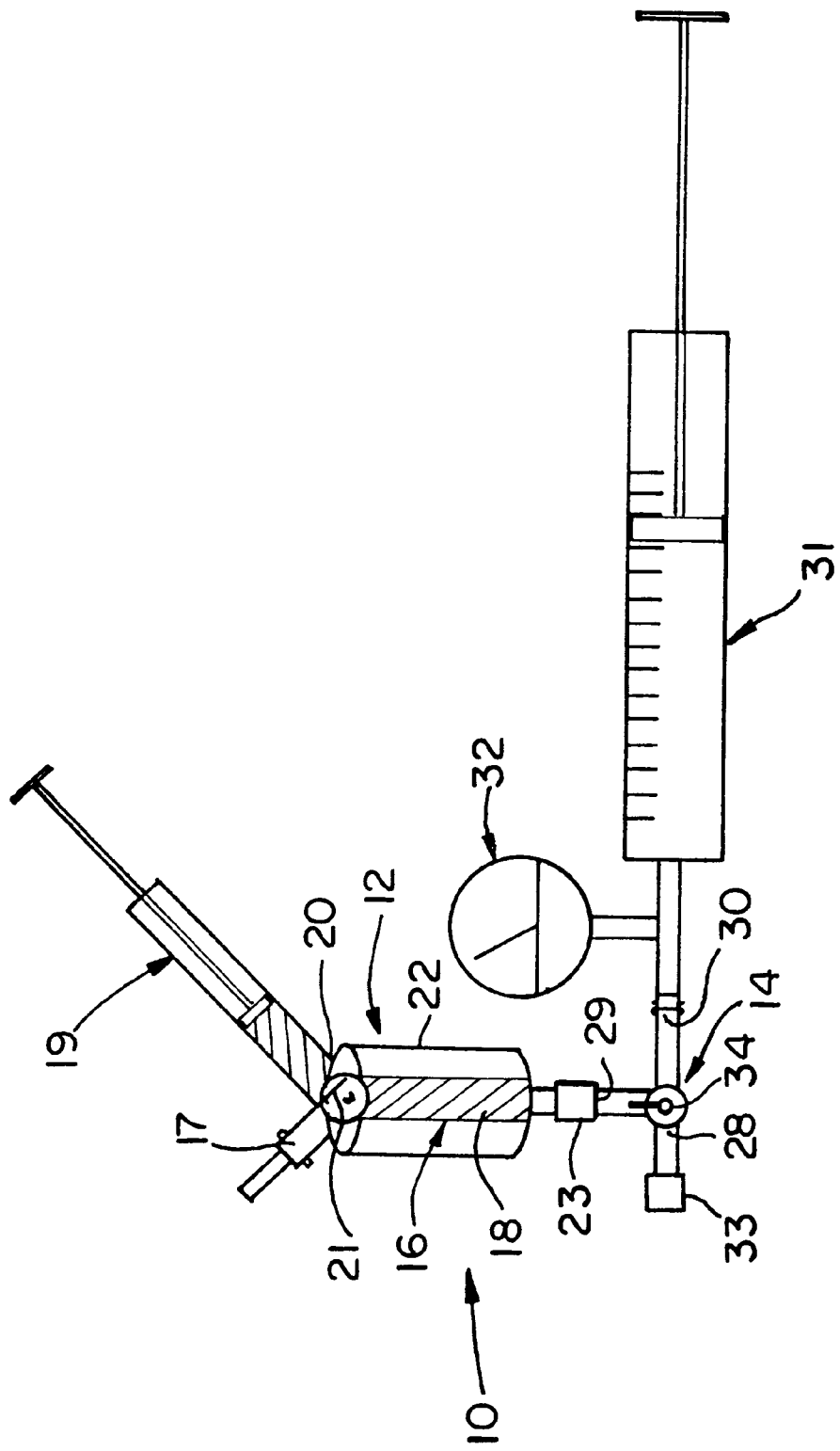
FIG. 1 is a schematic, side-elevational view of a dosing apparatus for treating a body structure with radiation in accordance with the present invention.

A dosing apparatus for treating a body structure, such as an artery or vein, in accordance with the present invention is depicted schematically in FIG. 1. The dosing apparatus 10 is used for preparing an appropriate dose of a radioactive solution to treat the desired body structure. In addition, the dosing apparatus 10 enables the radioactive solution to be efficiently transferred from a radioisotope generator to a balloon of a catheter and guide wire assembly without exposing the user to a serious risk of direct contact with the radioactive solution. As shown in FIG. 1, the dosing apparatus 10 comprises a concentrator 12 and a delivery unit 14 in the form of a T-connector.

Since the output volumes of typical radioisotope generators (2–10 mL) may exceed the in-balloon volume of commonly used coronary and peripheral angioplasty balloons (up to 8 mL), the concentrator 12 is provided to enable substantially all of the radioactive material to be concentrated in a radioactive solution having an appropriate volume. The concentrator 12 comprises a generally cylindrical cartridge 16 having a hollow cavity or chamber. A first inlet 17 is provided for establishing a fluid communication between the cavity of the concentrator 12 and a radioisotope generator. The first inlet 17 enables the radioactive solution produced by the generator to flow directly from the generator into the cavity of the concentrator 12.

The cartridge 16 is filled with a separating medium 18 such as an ion-exchange resin. The separating medium 18 is selected to preferentially bind the radioactive material of the radioactive solution while allowing the solvent to pass through the separating material 18. The solvent may then be removed from the cartridge. The separating material 18 is also selected to enable the radioactive material to be eluted from the separating material 18 with a suitable elution fluid. In order to effectively elute the radioactive material from the separating material 18, a syringe 19 is attached to the concentrator 12 via a second inlet 20. The second inlet 20 is provided with a gate 21 which is biased to prevent fluid from leaking out of the concentrator 12 through the second inlet 20.

A shield 22 is provided to protect persons in close proximity to the concentrator 12 from exposure to radiation. In particular, the shield 22 protects the hands and fingers of any person handling the dosing apparatus 10 from radiation. Towards that end, the shield 22 is manufactured from a material which is capable of blocking the transmission of radiation, such as lead for blocking gamma ray radiation and/or plexiglass for absorbing radiation associated with positron emission. Further, for optimal performance, the shield 22 should substantially surround and contain the concentrator 12 to insure that the maximum amount of radiation is blocked.

The concentrator 12 is connected to the delivery unit 14 through an outlet 23 of the cartridge 16 of the concentrator 12. The delivery unit 14 comprises a T-path fluid conduit 28 having a first inlet 29 for connecting the fluid conduit 28 to the outlet 23 of the cartridge 16. The fluid conduit 28 further comprises a second inlet 30 for connecting a pressure syringe 31 to the fluid conduit 28. A pressure gauge or manometer 32 is operatively connected between the pressure syringe 31 and the fluid conduit 28 for measuring the pressure of fluid contained within the pressure syringe 31. The fluid conduit 28 also comprises an outlet 33 for connecting the fluid conduit 28 to a catheter and guide wire assembly. Since the fluid within the fluid conduit 28 will be pressurized, each of the first inlet 29, the second inlet 30, and the outlet 33 are provided with a pressure controlling seal, such as a Luer lock seal. A three-way valve 34, such as a standard three-way stopcock, is provided on the fluid conduit 28 to enable the outlet 33 of the fluid conduit 28 to be connected to either the first inlet 29 or the second inlet 30, or to be isolated from both the first and second inlets, 29 and 30.

Figure 2:
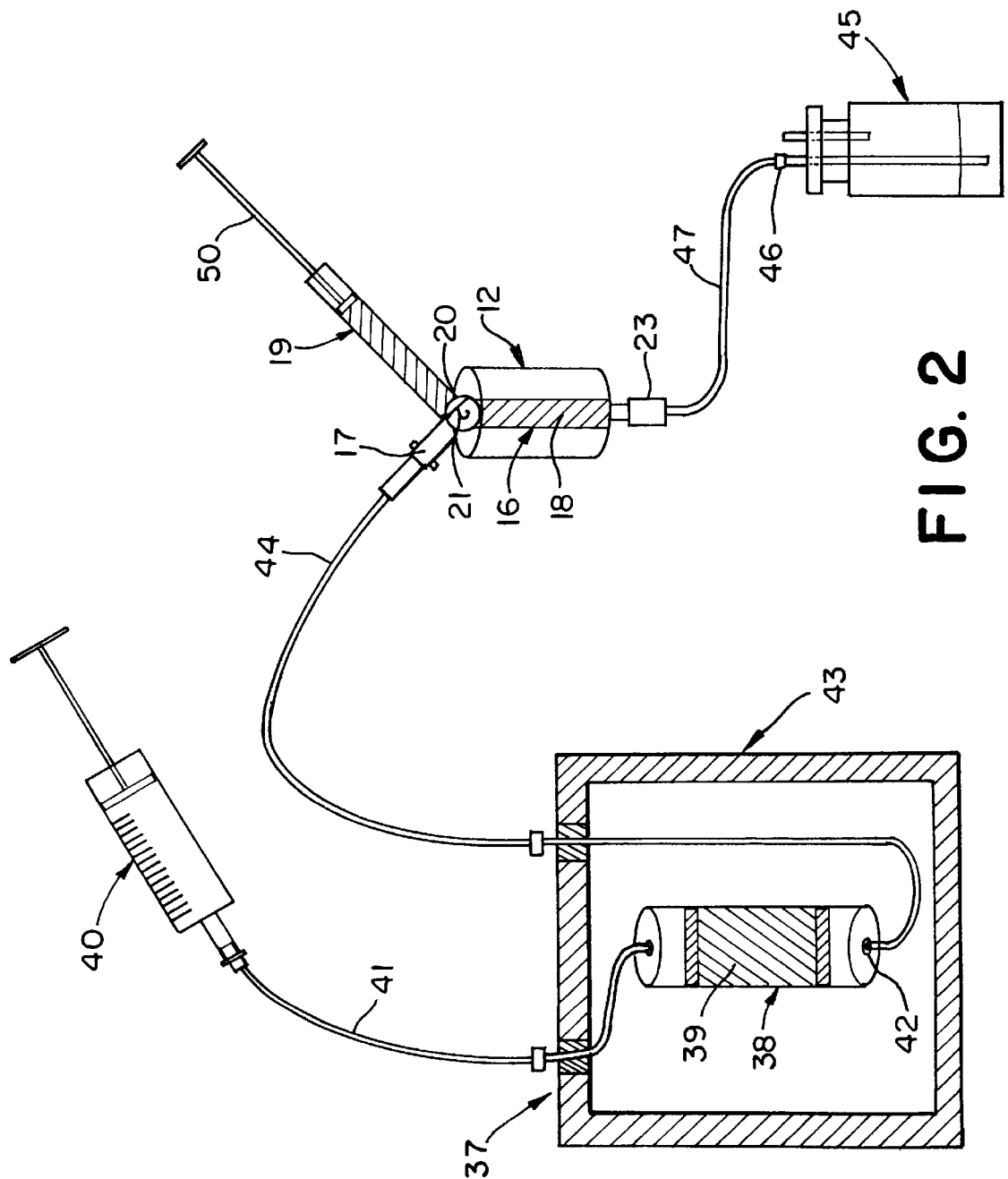
FIG. 2 is a schematic, partial cross-sectional, side-elevational view of the dosing apparatus depicted in FIG. 1 shown attached to a radioisotope generator and a waste container.

To treat the desired body structure with radiation using the dosing apparatus 10, the concentrator 12 is connected to a radioisotope generator 37 as shown in FIG. 2. The radioisotope generator 37 comprises a cartridge 38 having an interior chamber which is packed with an ion-exchange resin 39. A long-lived mother-nuclide is physically or chemically bound to the ion-exchange resin. The mother-nuclide constantly produces short-lived daughter-nuclides by physical decay. Since the daughter-nuclide represents a chemically different species from the mother-nuclide, the ion-exchange resin 39 used can be selected such that the daughter-nuclide is not effectively bound to the ion-exchange resin 39. The daughter-nuclide can therefore be eluted from the ion-exchange resin 39 by a dedicated fluid or eluent, typically a physiologic NaCl or HCl solution. Accordingly, the radioisotope generator 37 functions to generate a radioactive solution containing a radioisotope dissolved in a solvent. It will be appreciated that the volume of the interior chamber of the cartridge 38 may preferably be as small as possible in order to increase the concentration of the radioisotope in the radioactive solution.

The generator 37 further comprises a syringe 40 in fluid communication with the interior chamber of the cartridge 38 via tubing 41. Accordingly, the syringe 40 can be used to flush the ion-exchange resin 39 with the eluent. In one particular embodiment, the syringe 40 may be a conventional microprocessor controlled syringe pump to precisely define the eluted volume from the generator 37, as described below. The generator 37 is also provided with an outlet 42 to enable the radioactive solution to exit the cartridge 38. In addition, the generator 37 typically comprises a radiation shield 43 surrounding the cartridge 38 to protect persons in proximity to the generator 37 from excessive exposure to radiation. As shown in FIG. 2, fluid communication can be established between the generator 37 and the concentrator 12 by connecting the outlet 42 of the generator 37 with the first inlet 17 of the concentrator 12 with, for example, a flexible tube 44.

In one embodiment, the generator 37 comprises a $^{82}$Sr/$^{82}$Rb generator for the production of a solution containing $^{82}$Rb. The generator, which is commercially available (Squibb), has a useful lifetime of about one month and can be eluted every two hours to produce 2–10 mL of solution. Taking into account the mean and maximum positron energies of $^{82}$Rb (1.5 and 4.4 MeV, respectively), an activity between 10 and 50 mCi would provide a therapeutic dose of radiation (e.g., about 10–30 Gy at a prescription point which is 1 mm deep into the vessel wall) in 2–5 minutes. The daughter-nuclide, $^{82}$Rb, has a physical half-life of 1.4 minutes, which means that a radioactive spill would require maintaining a break of only 14 minutes (i.e., ten half-lives), after which work could resume without any need for a decontamination step or other special clean-up. In addition, the extremely short half-life of $^{82}$Rb effectively eliminates the problem of patient radio-intoxification in the event of balloon failure since the whole-body dose of radiation delivered to the patient would only be about 1–2 radiation equivalents for men (rem).

In an alternate embodiment, the generator 37 comprises a $^{68}$Ge/$^{68}$Ga generator for the production of a solution containing $^{68}$Ga. The generator, which is commercially available (DuPont-Merck), yields an eluate of $^{68}$Ga in 1N HCl. The frequency of elution is about the same as that for the $^{82}$Rb generator, however, the generator can be effectively used for as long as nine months. Due to the longer half-life of $^{68}$Ga as compared to $^{82}$Rb, a laboratory break of up to about 15 hours would be required in case of a spill. However, only 10–30 mCi would be sufficient to deliver 10–30 Gy at a prescription point which is 1 mm deep into the vessel wall within 1–15 minutes. Further, a patient would suffer a whole-body dose of less than about 5.0 rem upon balloon rupture.

In yet another embodiment, the generator 37 comprises a $^{188}$W/$^{188}$Re generator for the production of a solution containing $^{188}$Re. Considering the mean and maximum beta energies of $^{188}$Re (0.8 and 2.1 MeV, respectively), the use of $^{188}$Re in an angioplasty balloon would be feasible under similar conditions as those for $^{68}$Ga. However, a shut-down of about 7 days would be required in the event of a spill due to the longer half-life of $^{188}$Re.

The choice of generator 37 for a given application will be dependent upon other considerations, in addition to the desire to have a short shut-down period and the need to insure the safety of the patient and user. Since $^{68}$Ga and $^{188}$Re have a dose half-depth into vascular tissue of about 0.5–1.5 mm, $^{68}$Ga and $^{188}$Re are appropriate for irradiating the entire depth of a diseased coronary vessel wall, which can have a thickness of up to 5 mm. This suggests, however, that for vessels with walls significantly thinner than 5 mm, structures surrounding the body structure being treated may be irradiated. But, this will not present a problem when there are no critical radiosensitive structures surrounding the body structure being treated. For example, no structures of relevant radiosensitivity are typically around the coronary arteries.

In addition to connecting the concentrator 12 to the generator 37, fluid communication between the concentrator 12 and a waste container 45 is established. The fluid communication is established by connecting the outlet 23 of the concentrator 12 to an inlet 46 of the waste container 45 via a flexible tubing 47.

APPARATUS OPERATION

With the concentrator 12 connected to the generator 37 and the waste container 45 as shown in FIG. 2, the syringe 40 is operated to force the eluent through the cartridge 38 thereby flushing the ion-exchange resin 39 with eluent. As the eluent passes through the cartridge 38 and exits through the outlet 42, the daughter-nuclide is carried along with the eluent into the cartridge 16 of the concentrator 12. The gate 21, which is biased to seal the second inlet 20 of the concentrator 12, prevents fluid from exiting the concentrator 15 through the second inlet 20. The radioactive solution is maintained within the cartridge 16 for a sufficient period of time for substantially all of the daughter-nuclide to adsorb onto the separating medium 18 before the syringe 19 is used to flush the eluent from the cartridge 16. The plunger 50 of the syringe 19 is depressed causing an elution fluid contained within the syringe 19 to force the gate 21 to a position which blocks and seals the first fluid inlet 17 to prevent back flow of fluid through conduit 44 and which unblocks the second inlet 20 of the concentrator 12 to enable fluid communication between the syringe 19 and the cartridge 16. The injected elution fluid displaces the eluent by forcing the eluent from the cartridge 16 through the outlet 23 and into the waste container 45, where the eluent and any residual radioisotope contained therein can be stored or safely discarded. Preferably, the plunger 50 is depressed to a first resistance point which signals the user that a sufficient volume of elution fluid has been discharged from the syringe 19 to adequately displace the eluent. The volume capacity of the syringe 19 should be selected so that sufficient elution fluid remains in the syringe 19 after the initial flushing caused by movement of the plunger to the first resistance set point to enable subsequent filling of a balloon catheter with a desired amount of fluid.

Figure 3:
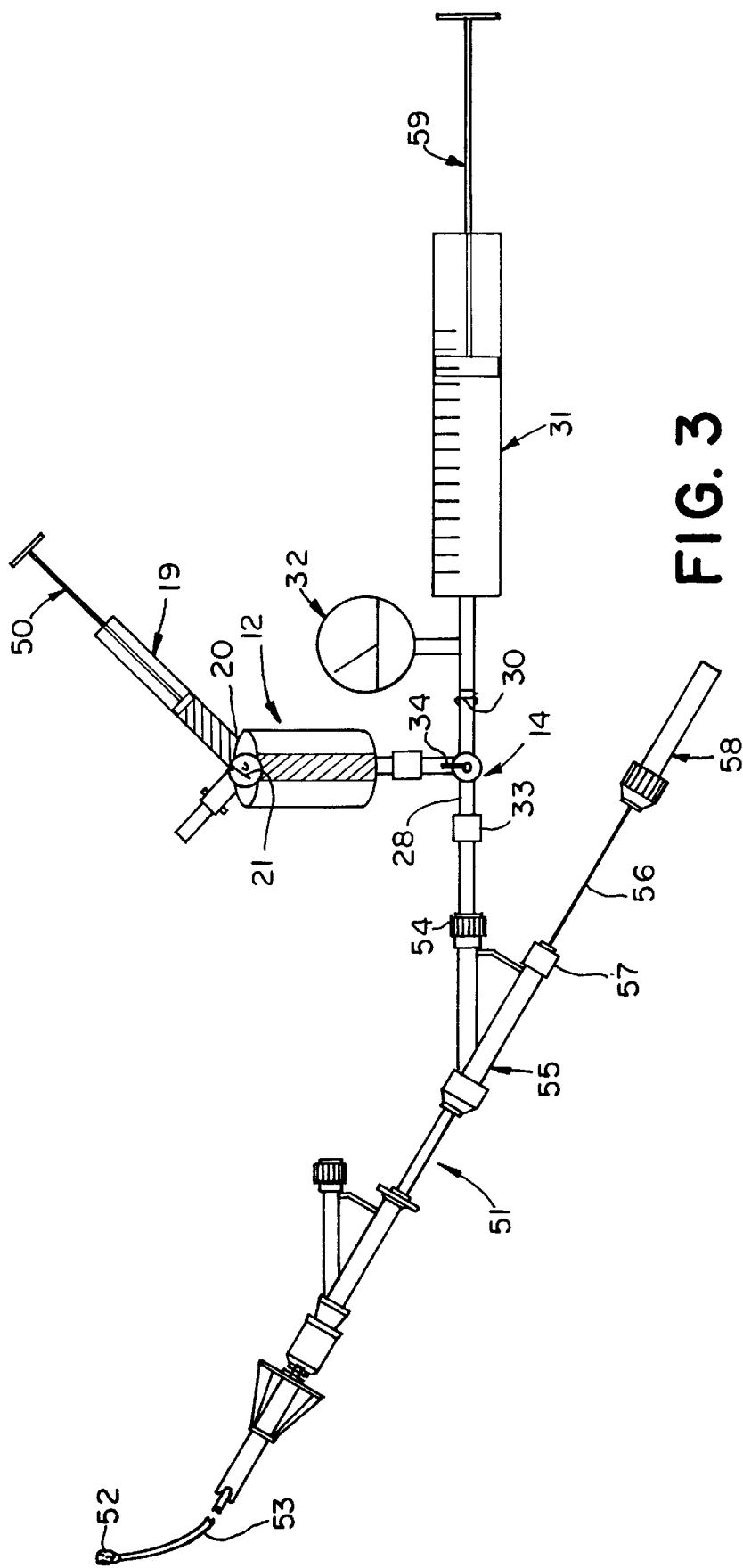
FIG. 3 is a schematic, partial, side-elevational view of the dosing apparatus depicted in FIG. 1 shown connected to a catheter and guide wire assembly.

With the radioisotope loaded onto the resin 18 of the concentrator 12, the concentrator 12 is disconnected from the generator 37 and the waste container 45. The concentrator 12 is then attached to the delivery unit 14, which is in turn connected to a catheter and guide wire assembly 51, as shown in FIG. 3, so that the radioisotope can be transferred to a balloon 52 at the distal end of the catheter and guide wire assembly 51. At this point, the valve 34 should be positioned so that the outlet 33 is connected to syringe 31 through the second inlet 30 of the fluid conduit 28. Since the balloon 52 can be accurately positioned along the body structure, the system is ideally suited for treating the body structure with radiation at a predetermined position along the body structure.

The catheter and guide wire assembly 51 comprises a flexible tube 53, having a lumen, with the balloon 52 positioned over the distal end of the tube 53. Accordingly, the interior of the balloon 52 is in fluid communication with the lumen of the tube 53. The proximal end of the tube 53 is connected to the outlet 33 of the fluid conduit 28 via a first inlet 54 of a Y-connector 55. The tube 53 is connected to the outlet 33 such that the lumen of the tube 53 is in fluid communication with the outlet 33 of the fluid conduit 28.

The balloon 52 may be a standard angioplasty balloon. Alternatively, the balloon 52 may be a balloon specially designed for treating the body structure with radiation. The balloon 52 used for a particular application should have a length which is selected to insure that the entire length of the body structure being treated receives a sufficient dose of radiation. Since the radiation level is expected to drop off towards the ends of the balloon 52, the length of the deflated balloon 52 should be somewhat larger than the length of the section of the body structure being treated. If the length of the balloon 52 is too short, the ends of the segment being treated will not be properly dosed. As a result, the ends of the segment may restenose, thereby losing the benefits of the radiation treatment.

A guide wire 56 is insertable within the lumen of the tube 53 through a second inlet 57 of the Y-connector 55. The guide wire 56 comprises a solid or braided wire which is sufficiently flexible to guide the flexible tube 53 and balloon 52 through the body structure being treated. The tube 53 can be guided through the body structure and the balloon 52 can be positioned within the lumen of the body structure by manipulating the proximal end of the guide wire 56. Towards that end, the length of the flexible tube 53 is sufficient to enable the proximal end of the tube 53 to be accessible extracorporeally. A hand control or torquer 58 is provided to facilitate manipulation of the guide wire 56.

Before the radioactive solution can be introduced into the balloon 52 and, preferably, before the balloon 52 is placed at the predetermined position along or within the body structure, the balloon 52 should be evacuated to remove air bubbles, in a similar manner as is used in standard angioplasty techniques. Specifically, with the pressure syringe 31 disconnected from the second inlet 30 of the fluid conduit 28, the plunger 59 of the pressure syringe 31 is depressed to expel gas from the body of the pressure syringe 31. The plunger 59 of the pressure syringe 31 is then manipulated to withdraw gases from the balloon 52 by partially withdrawing the plunger 59 from the body of the pressure syringe 31.

In some applications, it may be useful to condition the balloon 52 by first inflating the balloon 52. In such cases, the plunger 59 of the pressure syringe 31 can be partially withdrawn from the body of the pressure syringe 31 prior to attaching the pressure syringe 31 to the fluid conduit 28. The pressure syringe 31 can then be attached to the fluid conduit 28 and the plunger 59 depressed in order to inflate the balloon 52. The plunger 59 can then be partially withdrawn to deflate the balloon 52. The balloon 52 can then be evacuated as described above.

The balloon 52 is then positioned within the lumen of the body structure. Towards that end, standard catheterization techniques are used to insert the tube 53 and balloon 52 within the body structure. The distal end of the tube 53 is then manipulated using the guide wire 56 and the hand control 58 to position the balloon 52 at the position along the segment of the body structure which is to be treated with radiation.

With the balloon 52 appropriately positioned within the body structure, the radioactive solution is transferred into the balloon 52. The valve 34 is switched to provide fluid communication between the catheter and guide wire assembly 51 and the concentrator 12. The vacuum within the balloon 52 should cause all or some of the radioactive solution within the concentrator 12 to be drawn into the catheter and guide wire assembly 51. In the event that all of the radioactive solution is not removed from the concentrator 12, as will be readily apparent by viewing the position of the plunger 50 of the syringe 19, the plunger 50 of the syringe 19 can be depressed to force the remaining radioactive solution into the catheter and guide wire assembly 51.

In order to insure that substantially all of the radioactive solution is contained in the balloon 52 at the distal end of the catheter and guide wire assembly 51, the pressure syringe 31 is disconnected from the fluid conduit 28, filled with a fluid, and re-attached to the second inlet 30 of the fluid conduit 28. The fluid may contain a contrast agent so that a fluoroscope could be used to insure that the catheter was properly positioned within the vessel being treated. However, it should be appreciated that, if the contrast agent enters the balloon 52, the contrast agent will dilute the radioactive solution thereby requiring a longer exposure time. Accordingly, the contrast agent is preferably confined to the catheter. Towards that end, in some applications, it may be preferable to use a fluid which is immiscible with the elution fluid, such as mineral oil. Alternatively, the fluid may be gaseous, such as carbon dioxide or air. The valve 34 is then switched to establish fluid communication between the pressure syringe 31 and the catheter and guide wire assembly 51. The plunger 59 of the pressure syringe 31 is depressed to force the fluid from the pressure syringe 31, thereby pushing the radioactive solution distally into the balloon 52. The plunger 59 is depressed a sufficient distance to insure that the balloon 52 expands to its specified outer diameter in order to bring the radioactive solution in close proximity to the body structure being treated. Towards that end, the pressure within the balloon 52 is monitored using the manometer 32. After the balloon 52 has been adequately filled, the balloon 52 is maintained within the body structure for a period of time sufficient to provide the desired dose of radiation to the body structure. After the body structure has been sufficiently dosed, the plunger 59 of the pressure 31 syringe is partially withdrawn from the body of the pressure syringe 31, thereby deflating the balloon 52. The balloon 52 is then withdrawn from the body structure. The balloon 52, tubing 53, delivery unit 14, and pressure syringe 31 can be disposed of as a sealed unit, to further reduce the risk of a radioactivity leak.

In light of the foregoing, it will be appreciated that the fluid space in the cartridge 16 of the concentrator 12 should be about the same as the volume of the balloon 52. For example, since a 3 cm long, 0.25 mm diameter autoprofusion balloon has a volume of about 0.35 cc, the fluid space in the cartridge 16 should also be about 0.25 cc when such a balloon is used. Further, the syringe 40 should have a volume which is at least as great as, and preferably at least five times as great as, the volume of the fluid space in the cartridge 38. The volume of the syringe 40 should be sufficiently large to account for the dead space which is created within the tubing 41 connecting the syringe 40 to the generator 37 and the tubing 44 connecting the generator 37 to the concentrator 12. Accordingly, for most applications, a syringe 40 having a volume of about 10 cc is sufficient. In addition, since the syringe 19 of the concentrator 12 is used to flush the resin 39 with the elution fluid twice, the volume of the syringe 19 is preferably at least twice the volume of the fluid space in the cartridge 16. Also, the plunger 50 of the syringe 19 preferably has a resistance set point when about half the volume of the syringe 19 has been discharged in order to prevent a user from discharging too much of the elution fluid when the eluent is being flushed from the concentrator 12.

Figure 4:
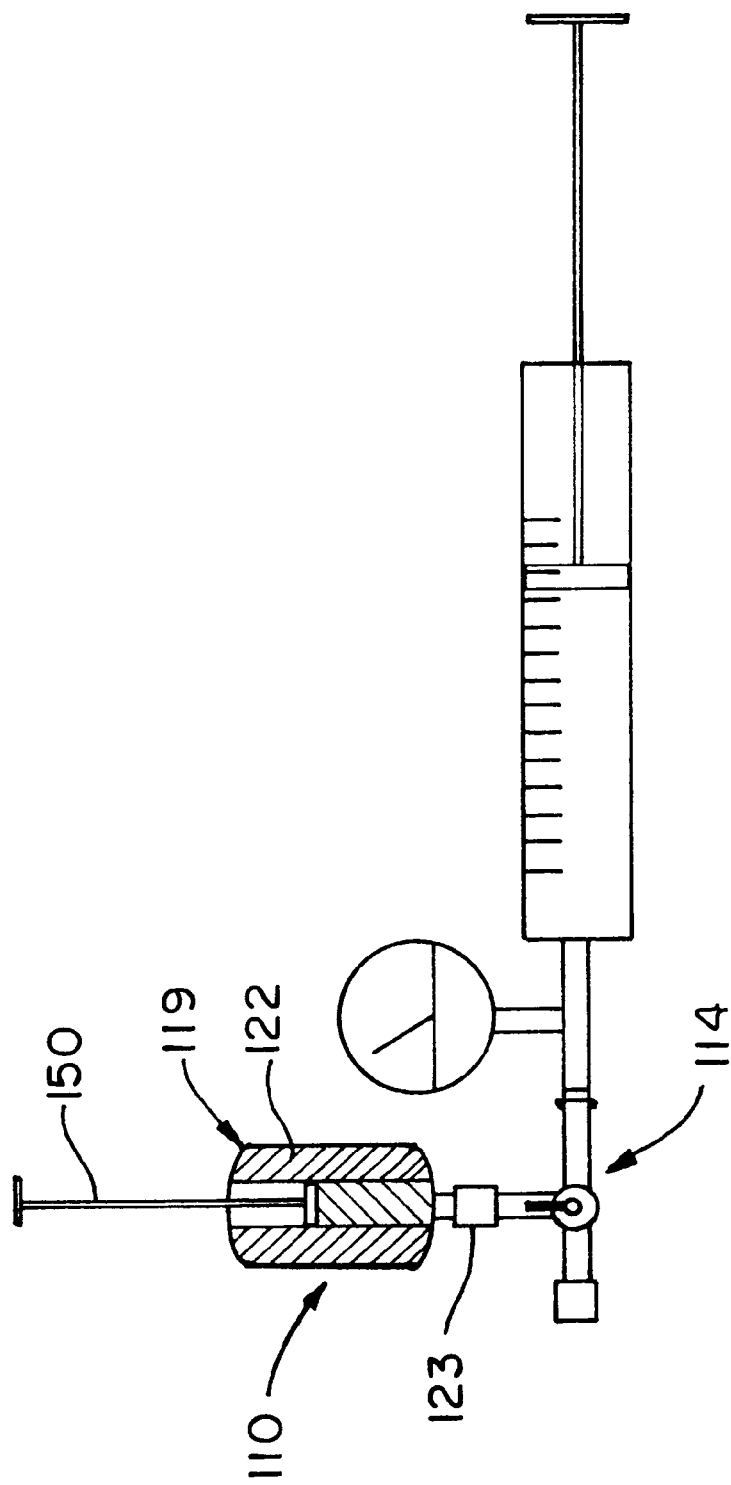
FIG. 4 is a schematic, side-elevational view of an alternate embodiment of the dosing apparatus for treating a body structure with radiation in accordance with the present invention.

An alternate embodiment of the dosing apparatus in accordance with the present invention is depicted schematically in FIG. 4. The dosing apparatus 110 is specifically designed for applications where the solution containing the radioactive material does not need to be concentrated prior to filling the balloon. The dosing apparatus 110 comprises a syringe 119 having a body with a generally cylindrical cavity. One end of the cavity incorporates a port 123. A plunger 150 is positioned within the other end of the cavity. A shield 122, similar to the shield 22 described in relation to dosing apparatus 10, is positioned about the syringe 119 to protect persons from exposure to radiation. The syringe 119 reversibly communicates through the port 123 with a delivery unit 114 in the form of a T-connector. The delivery unit 114 is substantially identical to the delivery unit 14 previously described in connection with dosing apparatus 10.

Figure 5:
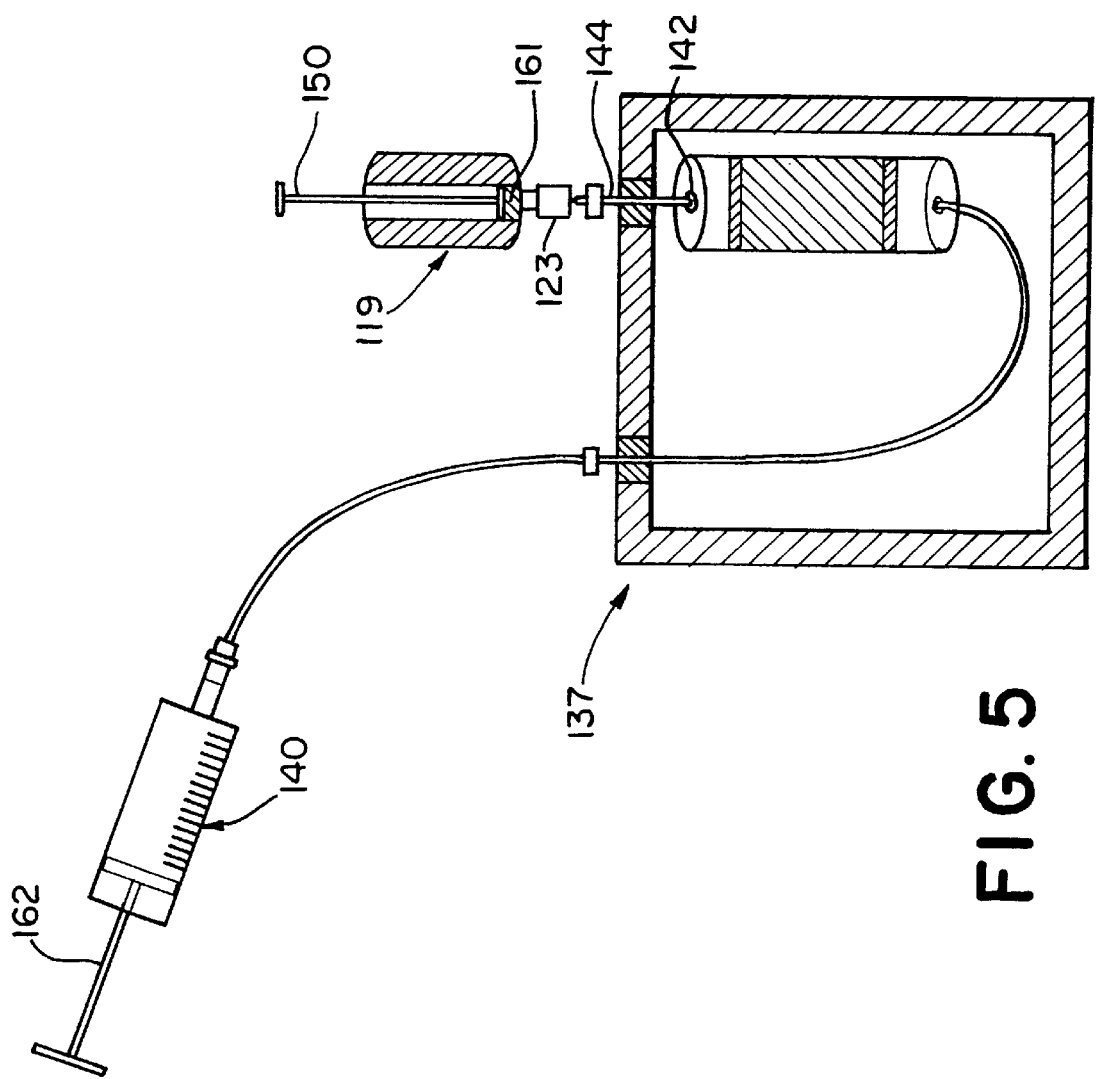
FIG. 5 is a schematic, partial cross-sectional, side-elevational view of the dosing apparatus depicted in FIG. 4 shown connected to a radioisotope generator.
Figure 6:
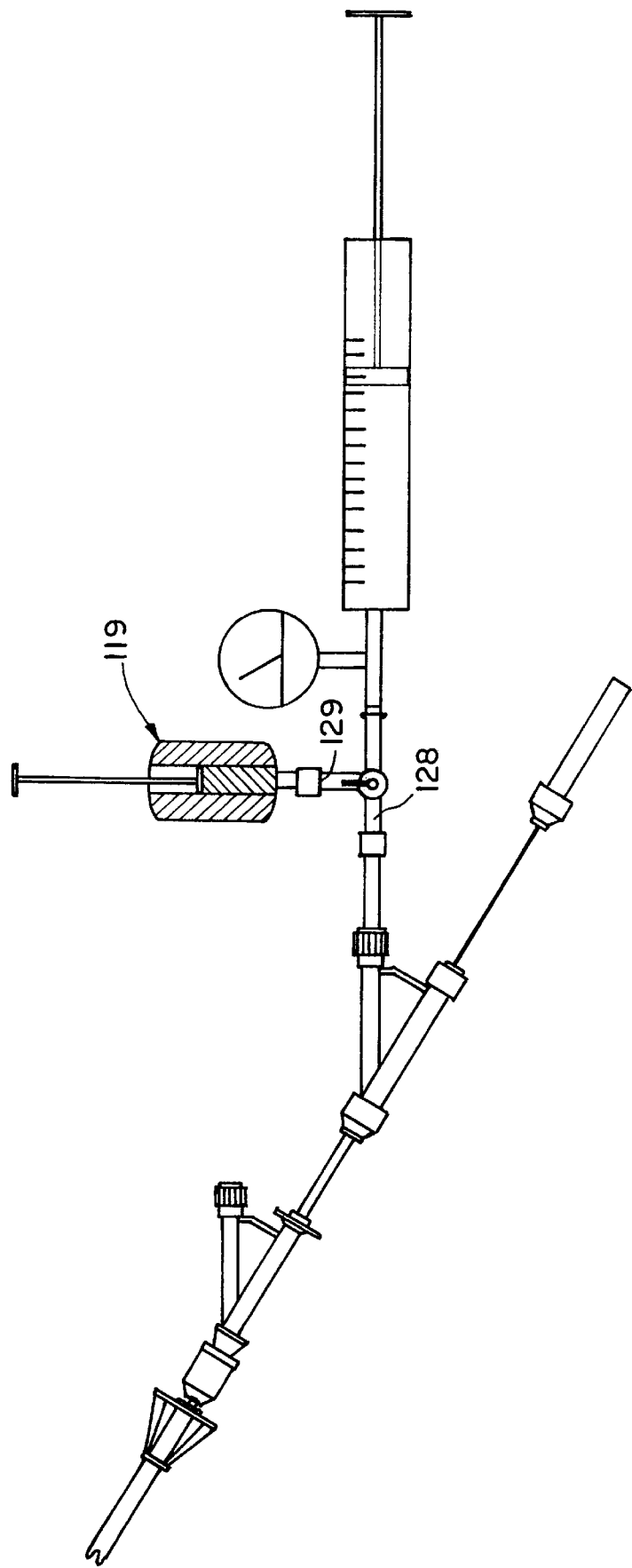
FIG. 6 is a schematic, partial, side-elevational view of the dosing apparatus depicted in FIG. 4 shown connected to a catheter and guide wire assembly.

In operation, the syringe 119 is first connected, as shown in FIG. 5, to a radioisotope generator 137, similar to one of the generators described above. Prior to connecting the syringe 119 to the generator 137, the plunger 150 is depressed, leaving only a small volume 161 within the body of the syringe 119. The small volume can be filled with a buffering fluid to neutralize the eluent from the generator 137. The syringe 119 is then connected to the generator 137 by connecting the port 123 of the syringe 119 to the outlet 142 of the generator 137 with flexible tubing 144. Reducing the length of tubing 144, minimizes the amount of dead space between the syringe 119 and the generator 137. The plunger 162 of the syringe 140 is then depressed within the body of the syringe 140 to force the radioactive solution from the generator 137 into the body of the syringe 119. Alternatively, the syringe 140 may be a microprocessor controlled syringe pump. As the radioactive solution enters the syringe 119, the pressure exerted by the solution on the plunger 150 causes the plunger 150 to be partially withdrawn from the body of the syringe 119. When a sufficient amount of radioactive solution has been filled within the syringe 119, the syringe 119 is detached from the generator 137. The syringe 119, with the radioactive solution contained therein, is then attached to the first inlet 129 of the fluid conduit 128 in the form of a T-connector, as shown in FIG. 6. The balloon is pre-conditioned, positioned within the body structure, filled with the radioactive solution, and discarded in an analogous manner as described above in relation to dosing apparatus 10.

Figure 7:
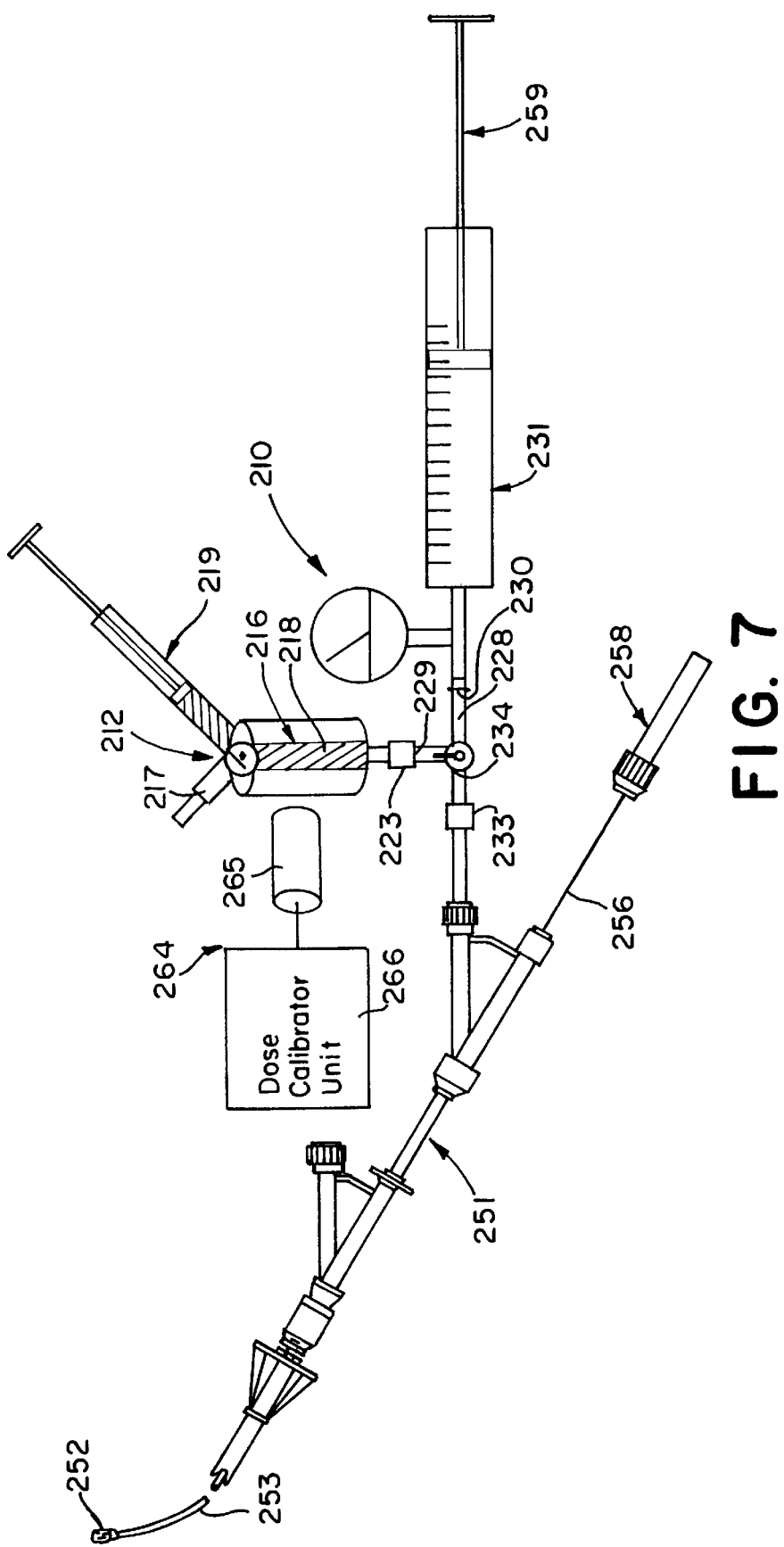
FIG. 7 is a schematic, side elevational view of another alternate embodiment of the dosing apparatus in accordance with the present invention shown connected to a catheter and guide wire assembly.

An alternate embodiment of the dosing apparatus is shown in FIG. 7. The dosing apparatus 210 is identical to the dosing apparatus 10 of FIG. 1 except that the dosing apparatus 210 further comprises a calibrator or dosimeter 264. The calibrator 264 is operatively positioned adjacent to the concentrator 212 to enable the calibrator 264 to measure the level of radioactivity associated with the radioactive material loaded onto the separating material 218 contained within the concentrator 212. The calibrator 264 comprises a counter 265, such as a standard or miniature Geiger-Müller counter, for directly measuring the radioactivity of the radioactive material. The counter 265 is positioned adjacent to the concentrator 212 so that the counter 265 can measure the radiation level of the radioactive material when the radioactive material is bound to the separating material 218. Accordingly, the counter 265 preferably measures the radiation level associated with the entire amount of radioactive material bound to the separating material 218. The calibrator 264 further comprises a dose calibrator unit 266 for determining the amount of time needed to expose the body structure being treated to the radiation in order to provide a therapeutic dose of radiation to the body structure (i.e., exposure time). For example, the dose calibrator unit 266 may comprise computer circuitry for calculating the exposure time necessary to provide a 10–30 Gy dose of radiation, at a prescription point 1 mm deep into the vessel wall, based on the size and volume of the balloon and the amount of radioactive material actually contained within the balloon. Accordingly, the dose calibrator unit 266 utilizes the measured level of radioactivity and, based on the decay rate of the radioactive material and the elapsed time between measurement of the radioactivity level and introduction of the radioactive solution into the balloon, signals the user as to the appropriate exposure time.

Figure 9:
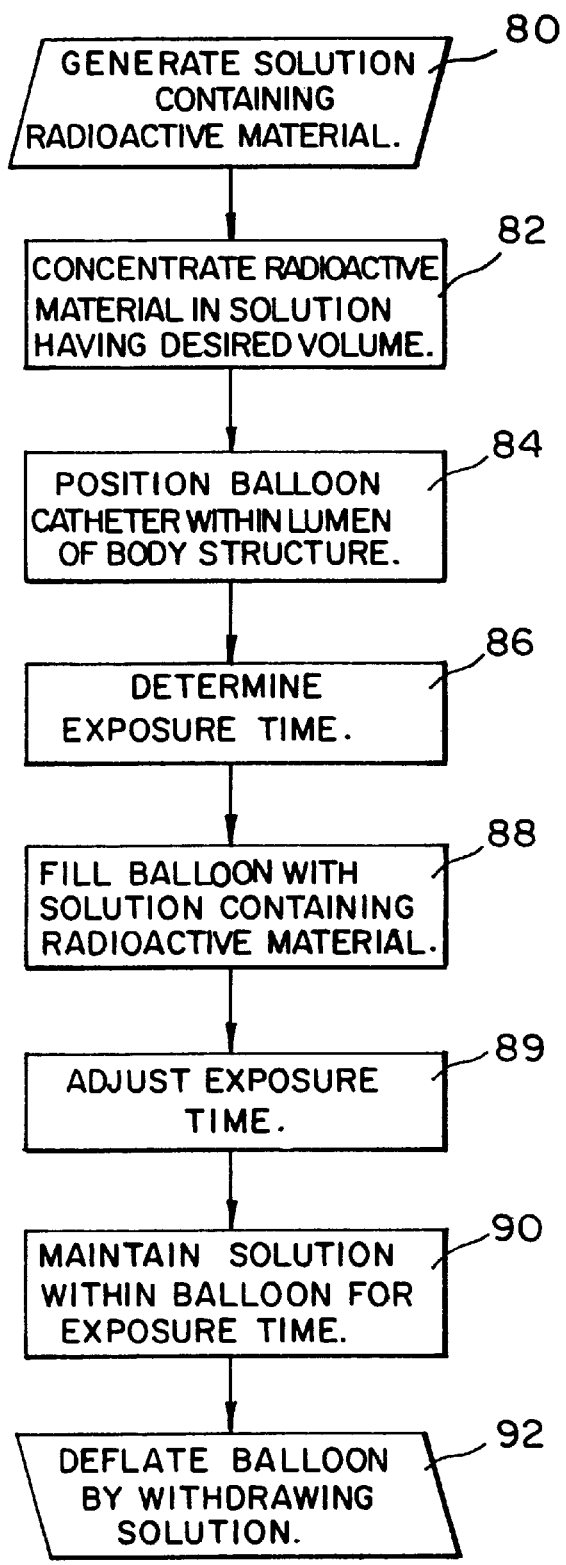
FIG. 9 is a flow chart depicting the steps of a method for treating a lumenal body structure with radiation in accordance with the present invention.

The dosing apparatus 210 shown in FIG. 7 can be used in a method for treating a lumenal body structure with radiation in much the same way as described above with reference to the dosing apparatus 10. Specifically, the method for treating a body structure using the dosing apparatus 210 is depicted in the steps of the flow chart shown in FIG. 9. At step 80, a radioisotope generator is used to produce a solution containing a radioactive material. Towards that end, the solution is preferably transferred directly from the generator to the first inlet 217 of the concentrator 212.

The concentration of radioactive material in the solution is adjusted at step 82. When the solution enters the cartridge 216 of the concentrator 212, the radioactive material selectively binds to the separating medium 218 contained within the cartridge 216. The non-radioactive material, however, is drained from the cartridge 216 and discarded. An elution fluid can then be used to elute the radioactive material from the separating medium. Accordingly, a concentrated solution comprising the radioactive material can be produced.

At step 84, the balloon 252 and tubing 253 are positioned within the body structure such as within the lumen of a body structure. The balloon 252 may need to be primed prior to use, in order to remove air bubbles. Accordingly, the pressure syringe 231 is used to provide either positive or negative pressure in order to inflate and deflate the balloon 252. The balloon 252 is deflated by withdrawing air from the balloon 252 with the pressure syringe 231. The balloon 252 and tubing 253 are then directed through the body structure using the hand control or torquer 258 to manipulate the guide wire 256 and position the balloon 252 at the position along the lumen of the body structure which is to be treated.

If desired, the exposure time needed to provide a therapeutic dose of radiation is determined at step 86. Towards that end, the concentration or radiation level per unit volume of the radioactive material is measured with the counter 265, while the radioactive material is bound to the separating medium 218. Once the radiation level has been measured, the exposure time is determined by the dose calibrator unit 266 by comparing the radiation level to the dose needed to effectively treat the body structure.

At step 88, the balloon 252 is filled with the solution containing the radioactive material. With the three-way valve 234 turned to provide fluid communication between the outlet 223 of the concentrator 212 and the first inlet 229 of the T-connector fluid conduit 228, the radioactive material is dissolved from the separating material 218 by the elution fluid contained in the syringe 219. The radioactive material dissolved in the elution fluid is also flushed by actuation of the syringe 219 from the cartridge 218 through the T-connector 228 and into the catheter 251. The pressure syringe 231 is then detached from the second inlet 230 of the fluid conduit 228, filled with a suitable fluid, and reconnected to the second inlet 230 of the fluid conduit 228. The three-way valve 234 is then turned to provide fluid communication between the second inlet 230 and the outlet 233 of the fluid conduit 228. The plunger 259 of the pressure syringe 231 is then depressed to inject the suitable fluid into the tube 253 thereby forcing the solution containing the radioactive material toward the distal end of the balloon 252.

If desired, the exposure time can be adjusted at step 89. The counter 265 is used to measure the residual level of radiation contained in the concentrator 212 after the available radioactive material has been flushed from the concentrator 212. In a preferred embodiment, the residual level of radiation contained in both the concentrator 212 and the catheter and guide wire assembly is determined in order to get an even more precise measurement of the level of radiation actually contained in the balloon 25 2. The level of radiation contained in the balloon 252 is then re-calculated by subtracting the residual level of radiation from the level of radiation measured prior to filling the balloon 252. The dose calibrator unit 266 then adjusts the exposure time accordingly. The solution is maintained in the balloon 252 for a period of time equal to the predetermined exposure time at step 90.

After the body structure has been treated for the desired length of time, the balloon 252 is deflated by removing the solution containing the radioactive material from the balloon 252 at step 92. The solution is removed from the balloon 252 by partially withdrawing the plunger 259 from the body of the pressure syringe 231. The pressure syringe 231, along with the concentrator 212, the delivery unit 214, the tube 253, the balloon 252, and the radioactive solution can then be safely discarded as a sealed unit.

Figure 8:
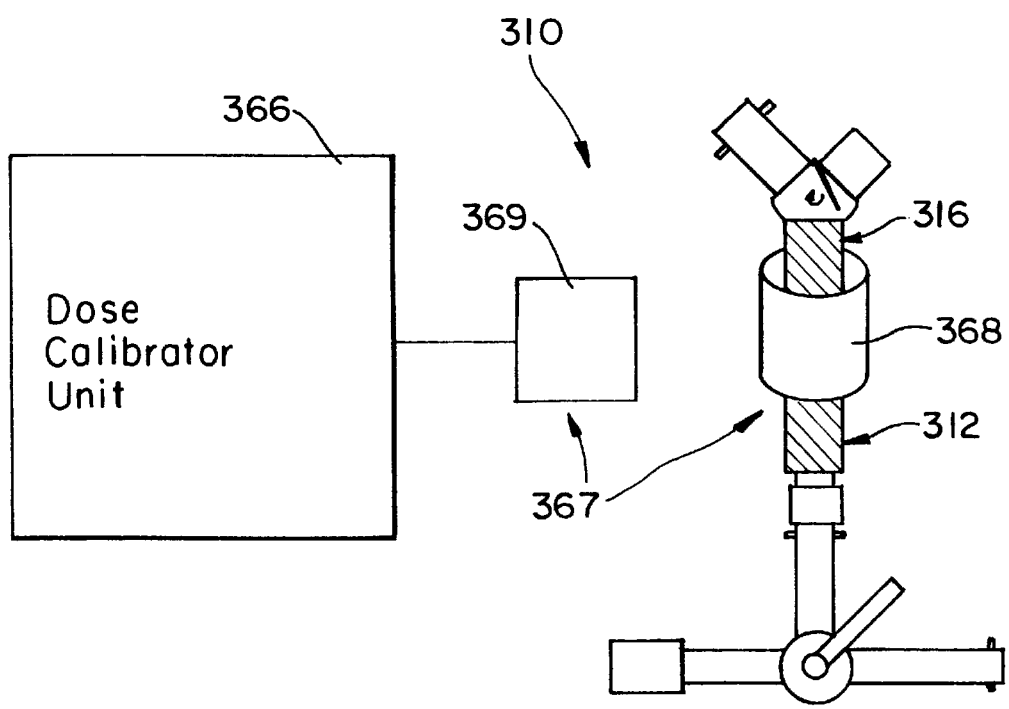
FIG. 8 is a schematic, side elevational view of yet another alternate embodiment of the dosing apparatus in accordance with the present invention.

Yet another embodiment of the dosing apparatus is depicted in FIG. 8. The dosing apparatus 310 of FIG. 8 is identical to the dosing apparatus 210 of FIG. 7 except that the Geiger-Müller counter 265 of the dosing apparatus 210 is replaced by a scintillation counter 367. The scintillation counter 367 comprises a cylindrical sleeve 368 which is positioned concentrically about the cartridge 316 of the concentrator 312. The sleeve 368 is manufactured from a scintillation material, such as a plastic scintillator, which produces light when struck by radiation. A photomultiplier tube 369 is operatively connected to the dose calibrator unit 366 and positioned adjacent to the sleeve 368 to allow the level of light produced by the sleeve 368 to be measured. Towards that end, the photomultiplier tube 369 may be connected to the sleeve 368 by a fiber optic light pipe.

Figure 10:
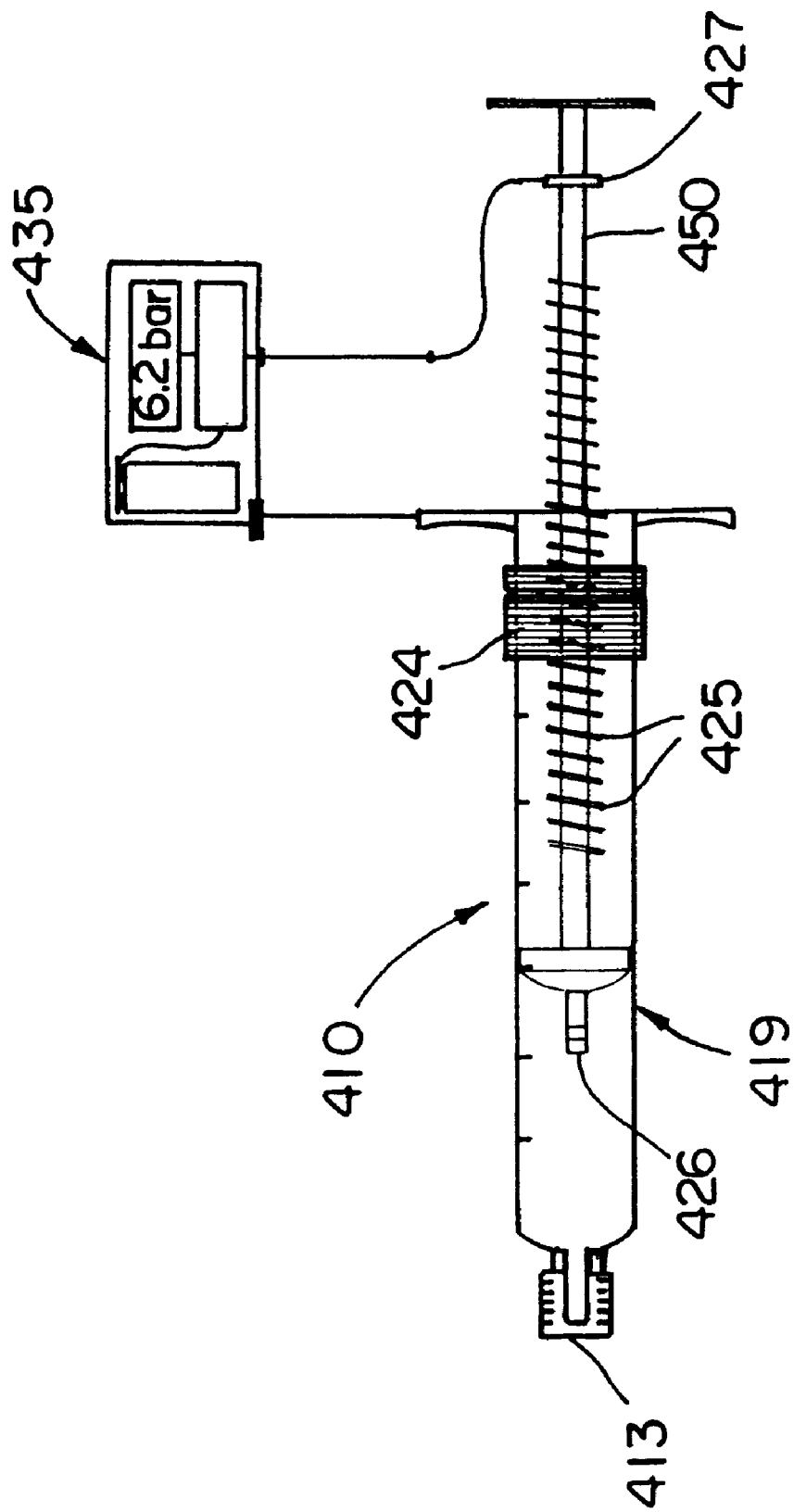
FIG. 10 is a schematic, side-elevational of another alternate embodiment of the dosing apparatus in accordance with the present invention.

Still another embodiment of the dosing apparatus in accordance with the present invention is depicted in FIG. 10. The dosing apparatus 410 comprises a pressurizable syringe 419 equipped with a Luer lock connector 413 at the front end of the syringe 419 to enable the syringe 419 to be removable attached to a radioisotope generator, a calibrator, or a catheter and guide wire assembly. The syringe 419 comprises a plunger 450 and a locking mechanism 424 which enables the plunger 450 to be moved within the body of the syringe 419 by freely advancing the plunger 450 within the syringe body when the locking mechanism 424 is in an unlocked position. The plunger 450 comprises external threads 425 which are sized to mate with internal threads provided along a central bore running axially through the locking mechanism 424. Accordingly, when the locking mechanism 424 is in a locked position, the plunger 450 can be advanced within the syringe body by rotating the plunger 450 to engage the external threads 425 of the plunger 450 with the internal threads of the locking mechanism 424, thereby axially translating the plunger 450. The plunger 450 further comprises a pressure transducer 426 integrally formed at the forward end of the plunger 450. Electrical cables extend from the transducer 426 through the plunger 450 toward the rear end of the plunger 450 where the cables are attached to a sliding clutch connector 427. The sliding clutch connector 427 enables the plunger 450 to be rotated without twisting the cables. The sliding clutch connector 427 is then detachably connected to a pressure meter 435 comprising electronic circuitry to operate the transducer 426, an alphanumeric display, and a power source such as a battery.

Figure 11:
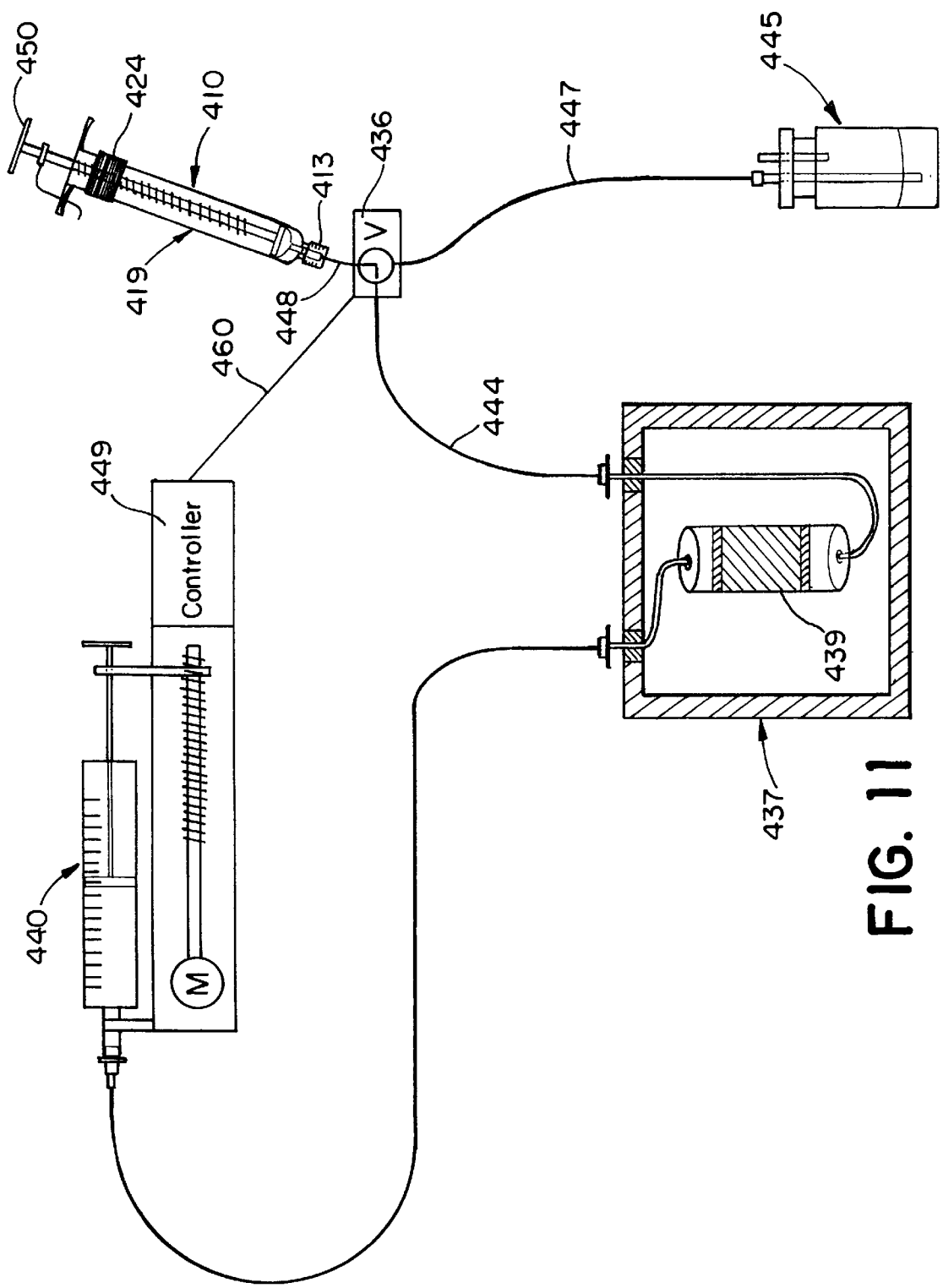
FIG. 11 is a schematic, partial cross-sectional, side-elevational view of the dosing apparatus depicted in FIG. 10 shown attached to a radioisotope generator and a waste container.

Use of the dosing apparatus 410 depicted in FIG. 10 will now be described. Referring to FIG. 11, a conventional microprocessor controlled syringe pump 440 is used to elute a radioactive solution from a radioisotope generator 437 directly into the dosing apparatus 410. The radioisotope generator 437 is substantially identical to the generator 37 described above with reference to FIG. 2. An outlet of the generator 437 is operatively connected to an input of an electrical switch valve 436 by a flexible tube 444. A first outlet of the valve 436 is connected to a waste container 445 by a flexible tube 447. The valve 436 is controlled by a controller 449 associated with the syringe pump 440 via an electrical cable 460.

The dosing apparatus 410 is then connected to a second outlet of the valve 436 by attaching the Luer lock connector 413 of the syringe 419 to a flexible tube 448 running between the dosing apparatus 410 and the valve 436. In order to minimize dead space between the dosing apparatus 410 and the valve 436, the length of the tube 448 is preferably as short as is conveniently possible. The locking mechanism 424 of the syringe 419 is then moved to an unlocked position so that the plunger 450 can move freely within the syringe body.

With the dosing apparatus 410 connected to the valve 436, the syringe pump 440 is started with the switch valve 436 in a position to allow fluid communication between the generator 437 and the waste container 445. The syringe pump 440 is activated by the controller 449 to advance a volume of eluent, equal to the functional volume between the generator 437 and the switch valve 436, into the waste container 445. The emptied volume is simultaneously filled with radioactive material in the eluent from cartridge 439. After the desired volume of eluent has been advanced, the controller 449 switches the valve 436 to a position allowing fluid communication between the generator 437 and the dosing apparatus 410. The syringe pump 440 is then operated to advance a precisely known volume of radioactive solution into the dosing apparatus 410.

The use of a microprocessor controlled syringe pump is particularly useful for controlled elution of peak radioactivity. It will be appreciated that the concentration of radioactive material within the radioactive solution being eluted from a generator is low as the radioactive solution first begins to exit the generator, reaches a peak value as the radioactive solution continues to be eluted from the generator, and decreases thereafter. Accordingly, the concentration of radioactive material within a dosing apparatus can be increased by operating the syringe pump to advance only the volume of radioactive solution having a concentration of radioactive material near the peak radioactivity into the dosing apparatus. In this regard, the eluent containing the initial lower radioactive material can be directed to the waste container until the higher level radioactive material reaches valve 436. At this point, the waste drainage is discontinued.

Figure 12:
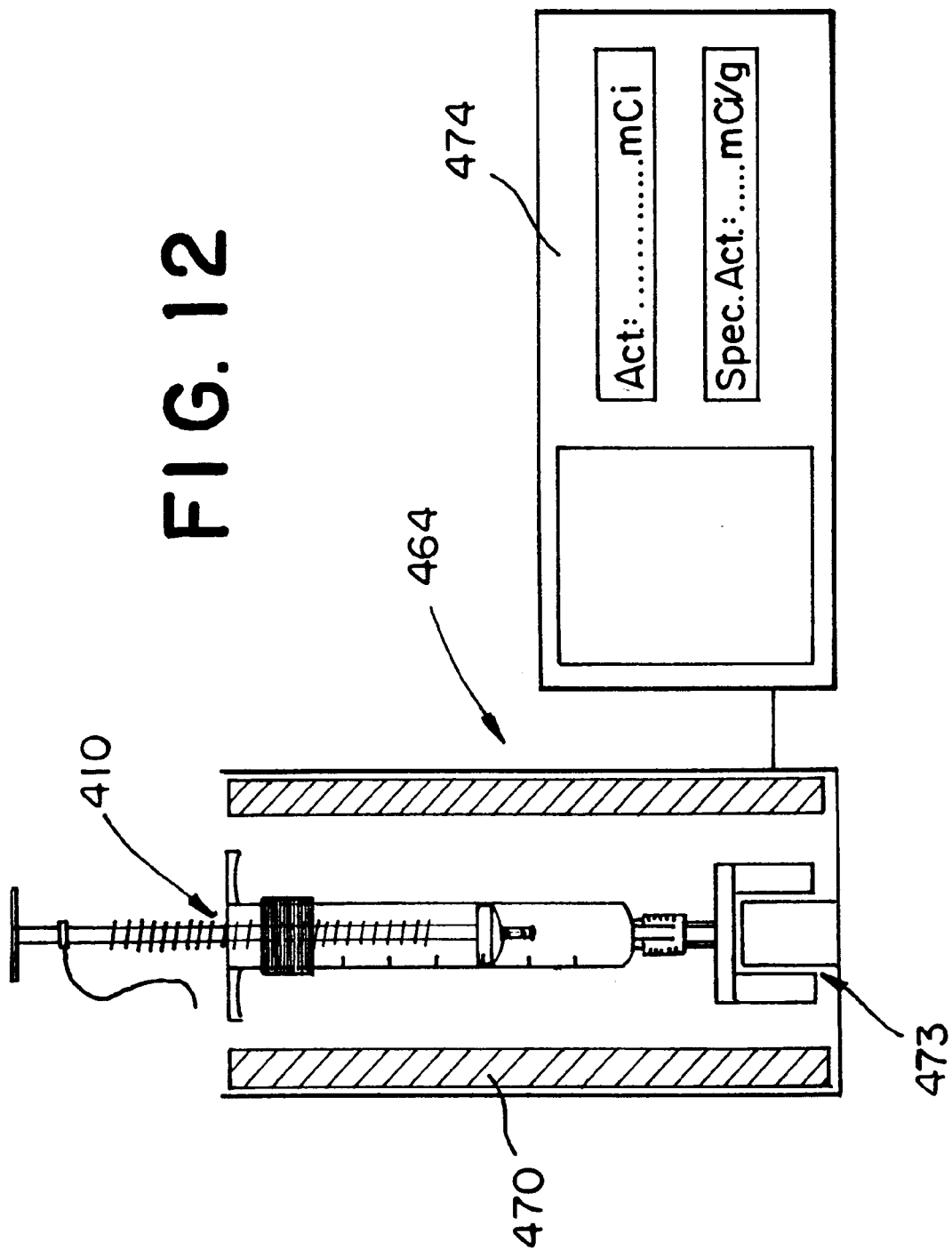
FIG. 12 is a schematic, partial cross-sectional, side-elevational view of the dosing apparatus depicted in FIG. 10 shown connected to a calibrator.

After the radioactive solution has been loaded into the dosing apparatus 410, the dosing apparatus 410 can be inserted into a holder 473 of a conventional dose calibrator 464, as shown in FIG. 12. For example, the calibrator 464 as shown comprises an ionization chamber 470 containing a counting gas which measures the activity of the radioactive solution contained within the dosing apparatus 410. Since the volume of the fluid contained within the dosing apparatus 410 is known, the specific activity and the exposure time can be determined. The specific activity and/or exposure time are then displayed on an alphanumeric display 474.

Figure 13:
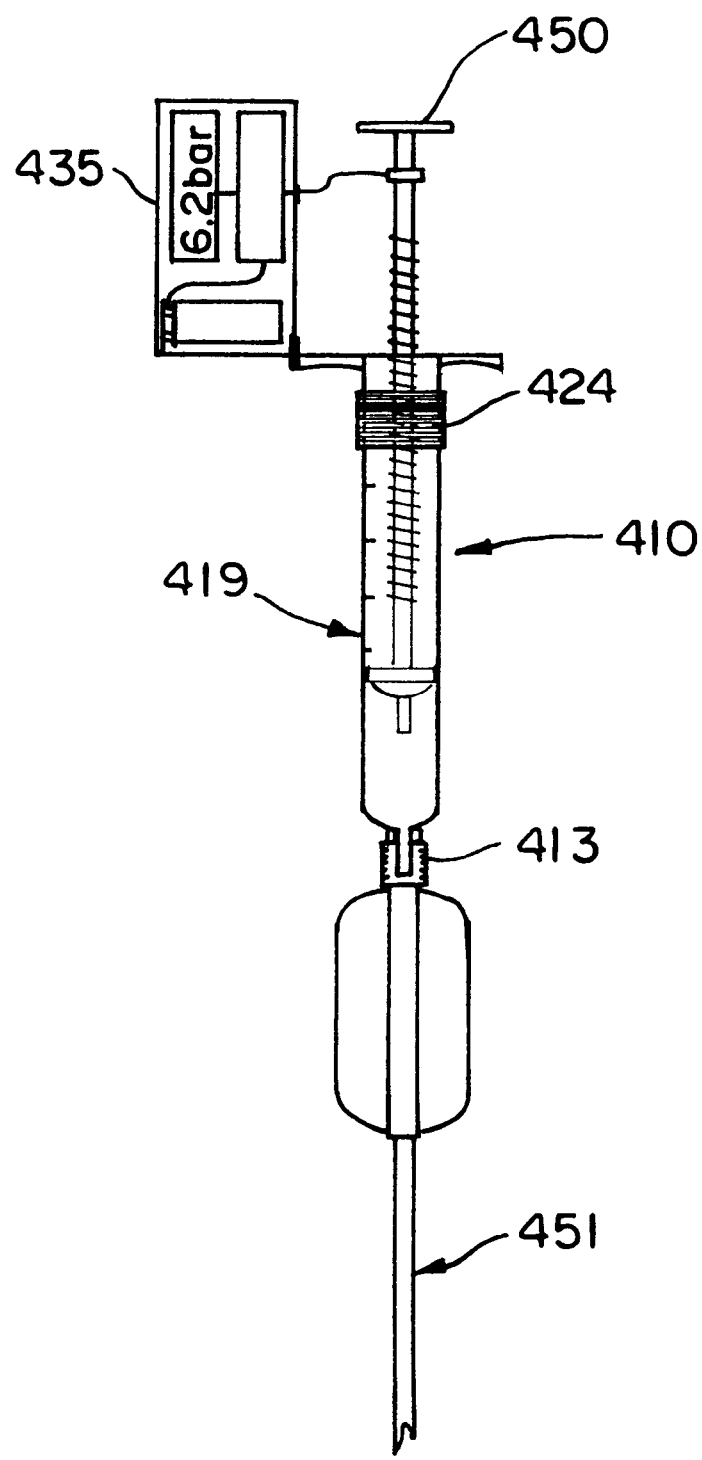
FIG. 13 is a schematic, partial cross-sectional, partial side-elevational view of the dosing apparatus depicted in FIG. 10 shown connected to a catheter and guide wire assembly.

As shown in FIG. 13, the dosing apparatus 410 is then attached to the proximal end of a balloon catheter 451 through the Luer lock connector 413 of the syringe 419. With the dosing apparatus 410 in an upright position, the plunger 450 is partially withdrawn from the syringe body to evacuate residual air from the catheter 451 and balloon. The evacuation of air is observed by watching air bubbles rise through the radioactive solution as the plunger 450 is withdrawn. The plunger 450 is withdrawn until essentially no more bubbles are seen. The locking mechanism 424 is then moved to a locked position and, if not already done, the pressure meter 435 is connected to the dosing apparatus 410. The radioactive solution is then advanced into the balloon by rotating the plunger 450. The plunger 450 is rotated until the pressure meter 435 registers the desired pressure.

When the dosing apparatus 410 is used, the level of radioactivity contained within the balloon can be directly measured. Towards that end, the radioactive solution is advanced into the balloon prior to inserting the balloon catheter 451 into the vessel being treated. A calibrator, such as calibrator 464 of FIG. 12, is then used to measure the level of radioactivity contained within the balloon. The radioactive solution is then withdrawn from the balloon and the balloon of the balloon catheter 451 placed at the desired position within the vessel to be treated. The radioactive solution is then reintroduced into the balloon and maintained within the balloon for a period time sufficient to provide a therapeutic dose of radiation to the vessel.

Figure 14:
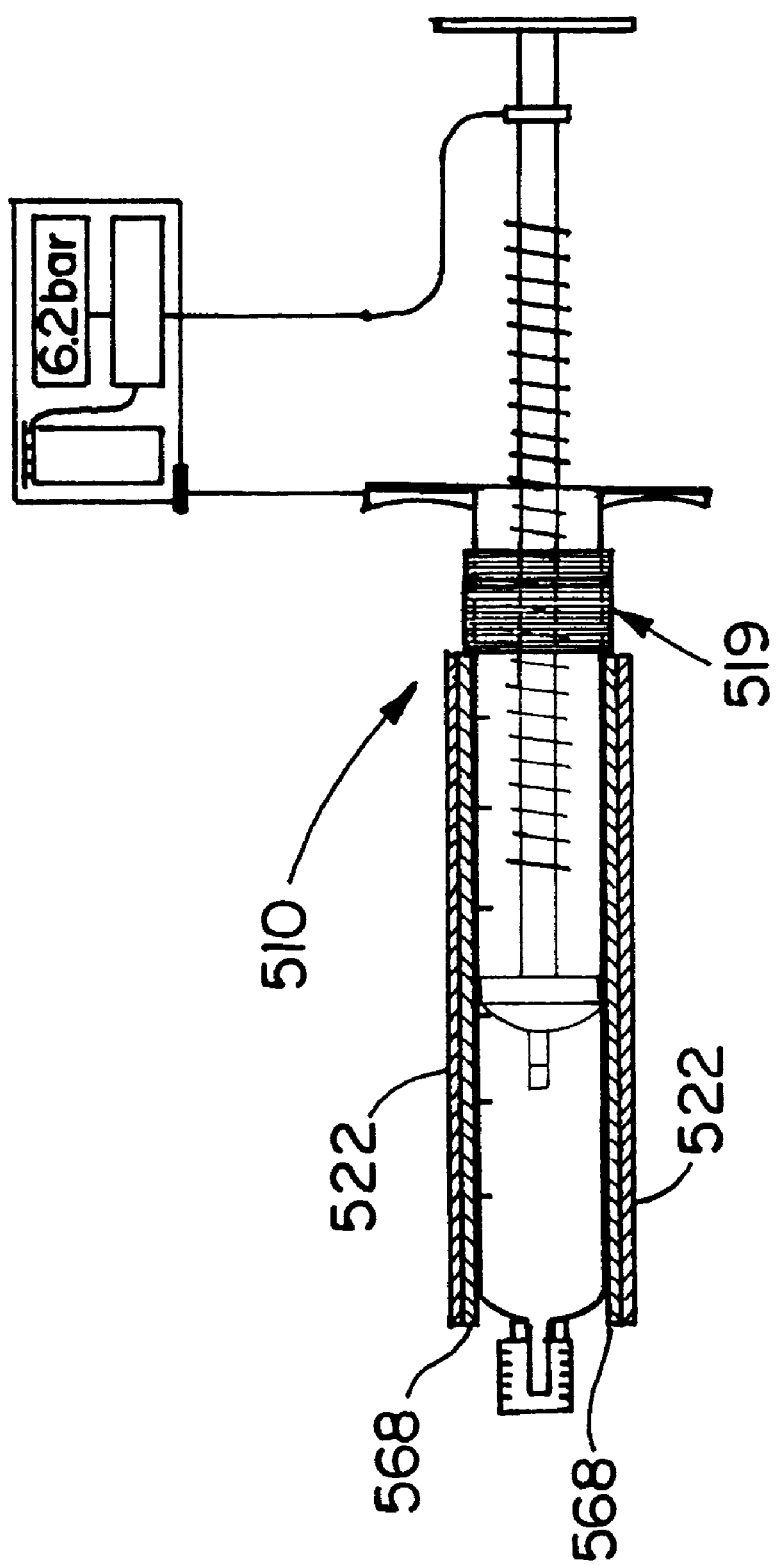
FIG. 14 is a further embodiment of the dosing apparatus in accordance with the present invention.

A further embodiment of the dosing apparatus in accordance with the present invention is depicted schematically in FIG. 14. The dosing apparatus 510 is essentially identical to the dosing apparatus 410 of FIG. 10 except that the dosing apparatus 510 further comprises a sleeve 568 which is integrally formed with the syringe 519 of the dosing apparatus 510. The sleeve 568 is formed of a plastic scintillating material which, in conjunction with an external photomultiplier tube, can be used to measure the level of radioactivity of the radioactive solution contained within the syringe 519. Further, the dosing apparatus 510 may comprise a shield 522 integrally formed with the syringe 519 and positioned such that the shield 522 does not shield the sleeve 568 from the radioactive solution contained within the syringe 519. The shield 522 functions to protect both the patient and the user from stray radiation.

The dosing apparatus 510 is operated in much the same manner as described above with reference to dosing apparatus 410. However, the level of radiation contained within the dosing apparatus 510 is measured using the sleeve 568 and associated photomultiplier tube, instead of a separate calibrator.

Although the present invention has been described generally with reference to the treatment of arteries and veins, the scope of the present invention is not limited to such applications. For example, the present invention is believed to be equally applicable when used in conjunction with or following balloon catheter procedures for recanalization in conditions such as coronary artery disease, benign prostatic hypertrophy, malignant disorders of various tissues available to tubular access, occlusions in peripheral or cardiac vasculature, clearing and restoring prostatic and other intrusions in the urethra, opening fallopian tubes, dilating esophagal structures, arterial or venous graft occlusion, and synthetic graft occlusions. Further, the present invention is believed to be useful in conjunction with a range of interventional processes, such as angioplasty (including the use of over-the-wire and monorail catheters), atherectomy, laser recanalization, laser angioplasty, stent placement (including arterial and interhepatic stents), thermal processes, and ultrasound processes. Additionally, the radioisotope generator used as part of the present invention encompasses cyclotrons for the production of $^{15}O$, $^{13}N$, $^{18}F$, and $^{11}C$, such as those used for positron emission tomography (PET) or a cyclotron specially designed for use as part of the present invention. And further, the concentrating function of the present invention is not limited to the use of an ion-exchange resin but includes the use of other concentrating techniques either alone or in combination with each other, such as evaporation, controlled elution of peak radiation, and adjustment of the concentration of mother nuclide in the radioactive material generator and/or the volume of the generator.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for treating a body structure with a radioactive material comprising:
   a. a concentrator for receiving a first solution comprising a radioactive material and for producing a second solution comprising the radioactive material, the second solution having a greater concentration of the radioactive material than the first solution; and
   b. a delivery unit operatively connected to the concentrator for transferring the second solution from the concentrator to a balloon.

2. The apparatus according to claim 1 wherein the radioactive material has a half-life of not more than about 2 days.

3. The apparatus according to claim 1 wherein the radioactive material comprises a positron emitter.

4. The apparatus according to claim 1 further comprising a calibrator operatively associated with the concentrator for measuring a level of radiation associated with the radioactive material.

5. The apparatus according to claim 4 wherein the calibrator comprises an instrument for directly measuring the level of radiation associated with the radioactive material.

6. The apparatus according to claim 5 wherein the instrument comprises a Geiger-Müller counter.

7. The apparatus according to claim 4 wherein the calibrator comprises a scintillation counter.

8. The apparatus according to claim 7 wherein the scintillation counter comprises a plastic scintillator for producing light in response to radioactivity emitted from the radioactive material and a photomultiplier tube for measuring the intensity of the light.

9. The apparatus according to claim 8 wherein the plastic scintillator comprises a sleeve of plastic scintillating material positioned about the concentrator.

10. The apparatus according to claim 1 further comprising a generator operatively connected to the concentrator for producing the first solution comprising the radioactive material.

11. The apparatus according to claim 10 wherein the radioactive material has a half-life of not more than about 2 days.

12. The apparatus according to claim 10 wherein the generator comprises a positron emitter generator for generating a positron emitter.

13. The apparatus according to claim 12 wherein the positron emitter generator comprises a parent-daughter generator having an ion-exchange resin.

14. The apparatus according to claim 12 wherein the positron emitter generator comprises a cyclotron.

15. The apparatus according to claim 12 wherein the positron emitter is selected from the group consisting of $^{68}Ga$, $^{188}Re$, $^{11}C$, $^{13}N$, $^{18}F$, $^{82}Rb$, and $^{15}O$.

16. The apparatus according to claim 1 wherein the delivery unit comprises a fluid conduit having a first inlet operatively connected to the concentrator.

17. The apparatus according to claim 16 wherein the fluid conduit further comprises a second inlet and a pressure syringe operatively connected to the second inlet.

18. The apparatus according to claim 16 wherein the fluid conduit further comprises an outlet for connecting the delivery unit to a balloon catheter.

19. The apparatus according to claim 1 wherein the concentrator comprises:
   a. a cartridge having a first open end, a second open end, and a hollow cavity formed between the first and second open ends, the cartridge comprising:
      i. a first inlet for introducing the first solution into the cavity through the first open end of the cartridge; and
   b. a separating medium contained within the cavity of the cartridge for increasing the concentration of the radioactive material.

20. The apparatus according to claim 19 wherein the separating medium comprises a material which selectively bonds to the radioactive material.

21. The apparatus according to claim 19 further comprising a syringe for flushing the separating medium with an elution fluid.

22. The apparatus according to claim 21 further comprising a valve operatively connected to the first open end of the cartridge, the valve comprising:
   a. a second inlet connected to the syringe; and
   b. a gate for alternately blocking and unblocking the second inlet, the gate being biased in a position to block the second inlet.

23. The apparatus according to claim 19 further comprising a calibrator operatively associated with the concentrator for measuring a level of radiation associated with the radioactive material.

24. The apparatus according to claim 23 wherein the calibrator comprises an instrument for directly measuring the level of radiation associated with the radioactive material.

25. The apparatus according to claim 24 wherein the instrument comprises a Geiger-Müller counter.

26. The apparatus according to claim 23 wherein the calibrator comprises a scintillation counter.

27. The apparatus according to claim 26 wherein the scintillation counter comprises a plastic scintillator for producing light in response to radioactivity emitted from the radioactive material and a photomultiplier tube for measuring the intensity of the light.

28. The apparatus according to claim 27 wherein the plastic scintillator comprises a sleeve of plastic scintillating material positioned about the cartridge.

29. The apparatus according to claim 28 wherein the sleeve is integrally formed with the cartridge.

30. The apparatus according to claim 19 wherein the delivery unit comprises a fluid conduit having a first inlet operatively connected to the second open end of the cartridge.

31. The apparatus according to claim 30 wherein the fluid conduit further comprises a second inlet and a pressure syringe operatively connected to the second inlet.

32. The apparatus according to claim 30 wherein the fluid conduit further comprises an outlet for connecting the delivery unit to a balloon catheter.

33. The apparatus according to claim 19 further comprising a radioisotope generator connected to the inlet of the cartridge.

34. The apparatus according to claim 33 wherein the radioisotope generator comprises a positron emitter generator for generating a positron emitter.

35. The apparatus according to claim 34 wherein the positron emitter generator comprises a parent-daughter generator having an ion-exchange resin.

36. The apparatus according to claim 34 wherein the positron emitter generator comprises a cyclotron.

37. The apparatus according to claim 34 wherein the positron emitter is selected from the group consisting of $^{68}$Ga, $^{188}$Re, $^{11}$C, $^{13}$N, $^{18}$F, $^{82}$Rb, and $^{15}$O.

38. A method for treating a body structure with a radioactive material comprising:
   a. a transfer step wherein a radioactive solution comprising a radioactive material having a short half-life is transferred directly from a generator to a dosing apparatus;
   b. a dosimetry step wherein a level of radiation associated with the radioactive material is measured and a desired exposure time is determined; and
   c. a treatment step comprising the steps of:
      i. positioning a balloon adjacent to the body structure at a position along the body structure which is to be treated with radiation;
      ii. transferring the solution directly from the dosing apparatus to the balloon; and
      iii. maintaining the solution within the balloon for the exposure time.

39. The method according to claim 38, further comprising a concentration step wherein the volume of the solution comprising the radioactive material is reduced to increase the concentration of the radioactive material in the solution.

40. The method according to claim 39, wherein the volume of the solution is reduced through evaporation.

41. A method for treating a body structure with a radioactive material comprising:
   a. a transfer step wherein a first solution comprising a radioactive material having a short half-life is transferred directly from a generator to a dosing apparatus;
   b. a concentration step wherein the radioactive material is removed from the first solution and the radioactive material is dissolved in a second solution, the volume of the second solution being less than the volume of the first solution;
   c. a dosimetry step wherein a level of radiation associated with the radioactive material is measured and a desired exposure time is determined; and
   d. a treatment step comprising the steps of:
      i. positioning a balloon adjacent to the body structure at a position along the body structure which is to be treated with radiation;
      ii. transferring the second solution directly from the dosing apparatus to the balloon; and
      iii. maintaining the second solution within the balloon for the exposure time.

42. A method for treating a body structure with a radioactive material comprising:
   a. a transfer step wherein at least a first solution comprising a positron emitter is transferred directly from a generator to a dosing apparatus;
   b. a dosimetry step wherein a level of radiation associated with the positron emitter is measured and a desired exposure time is determined; and
   c. a treatment step comprising the steps of:
      i. positioning a balloon adjacent to the body structure at a position along the body structure which is to be treated with radiation;
      ii. transferring the solution directly from the dosing apparatus to the balloon; and
      iii. maintaining the solution within the balloon for the exposure time.

43. The method according to claim 42, further comprising a concentration step wherein the volume of the solution comprising the positron emitter is reduced to increase the concentration of the positron emitter in the solution.

44. The method according to claim 43, wherein the volume of the solution is reduced through evaporation.

45. A method for treating a body structure with a radioactive material comprising:
   a. a transfer step wherein a first solution comprising a positron emitter is transferred directly from a generator to a dosing apparatus;
   b. a concentration step wherein the positron emitter is removed from the first solution and the positron emitter is dissolved in a second solution, the volume of the second solution being less than the volume of the first solution;

c. a dosimetry step wherein a level of radiation associated with the positron emitter is measured and a desired exposure time is determined; and d. a treatment step comprising the steps of:
  i. positioning a balloon adjacent to the body structure at a position along the body structure which is to be treated with radiation;
  ii. transferring the second solution directly from the dosing apparatus to the balloon; and
  iii. maintaining the second solution within the balloon for the exposure time.

46. The apparatus according to claim 1, wherein the volume of the second solution is less than the volume of the first solution.

47. The method according to claim 38, comprising the step of transferring a second solution from a pressure syringe to the dosing apparatus and wherein the treatment step comprises directing the second solution towards the balloon.

48. The method according to claim 47, wherein the second solution is immiscible with the radioactive solution.

49. The method according to claim 47, wherein the second solution contains a contrast agent.

50. The method according to claim 47, wherein the second solution is a gaseous fluid.

51. The method according to claim 41, comprising the step of transferring a third solution from a pressure syringe to the dosing apparatus and wherein the treatment step comprises directing the third solution towards the balloon.

52. The method according to claim 51, wherein the third solution is immiscible with the second solution.

53. The method according to claim 51, wherein the third solution contains a contrast agent.

54. The method according to claim 51, wherein the third solution is a gaseous fluid.

55. The method according to claim 42, comprising the step of transferring a second solution from a pressure syringe to the dosing apparatus and wherein the treatment step comprises directing the second solution towards the balloon.

56. The method according to claim 55, wherein the second solution is immiscible with the first solution.

57. The method according to claim 55, wherein the second solution contains a contrast agent.

58. The method according to claim 55, wherein the second solution is a gaseous fluid.

59. The method according to claim 45, comprising the step of transferring a third solution from a pressure syringe to the dosing apparatus and wherein the treatment step comprises directing the third solution towards the balloon.

60. The method according to claim 59, wherein the third solution is immiscible with the second solution.

61. The method according to claim 59, wherein the third solution contains a contrast agent.

62. The method according to claim 59, wherein the third solution is a gaseous fluid.

63. The apparatus according to claim 12, wherein the positron emitter generator is selected from the group of $^{82}Sr$, $^{68}Ge$, and $^{188}W$.

64. The apparatus according to claim 17, wherein the pressure syringe contains a third solution.

65. The apparatus according to claim 64, wherein the third solution is immiscible with the second solution.

66. The apparatus according to claim 64, wherein the third solution contains a contrast agent.

67. The apparatus according to claim 64, wherein the third solution is a gaseous fluid.

68. The apparatus according to claim 30, wherein the balloon has a volume substantially equal to a volume of the cavity of the cartridge.

69. The apparatus according to claim 19, wherein the separating medium is an ion-exchange resin.

70. The apparatus according to claim 21, wherein the elution fluid elutes the radioactive material from the separating medium.

71. The apparatus according to claim 21, wherein the elution fluid includes sodium chloride or hydrogen chloride solution.

72. The apparatus according to claim 13, wherein the ion-exchange resin does not bind the positron emitter.

73. The apparatus according to claim 10 comprising a syringe operatively connected to an inlet of the generator.

74. The apparatus according to claim 73, wherein the syringe is a microprocessor controlled syringe pump.

75. An apparatus for treating a body structure with a radioactive material comprising:
  a. a generator for receiving a first solution and for producing a second solution comprising a radioactive material;
  b. a receiving unit operatively connected to the generator for receiving the second solution from the generator; and
  c. a delivery unit operably connected to the receiving unit and adapted to transfer the second solution to a balloon.

76. The apparatus according to claim 75 comprising a calibrator operatively associated with the receiving unit for measuring a level of radiation associated with the radioactive material.

77. The apparatus according to claim 75 wherein the receiving unit is a syringe.

78. The apparatus according to claim 76 wherein the calibrator comprises an instrument for directly measuring the level of radiation associated with the radioactive material.

79. The apparatus according to claim 78 wherein the instrument comprises a Geiger-Müller counter.

80. The apparatus according to claim 76 wherein the calibrator comprises a scintillation counter.

81. The apparatus according to claim 80 wherein the scintillation counter comprises a plastic scintillator for producing light in response to radioactivity emitted from the radioactive material and a photomultiplier tube for measuring the intensity of the light.

82. The apparatus according to claim 81 wherein the plastic scintillator comprises a sleeve of plastic scintillating material positioned about the syringe.

83. The apparatus according to claim 75 wherein the radioactive material has a half-life of less than about 2 days.

84. The apparatus according to claim 75 wherein the generator comprises a positron emitter generator for generating a positron emitter.

85. The apparatus according to claim 84 wherein the positron emitter generator comprises a parent-daughter generator having an ion-exchange resin.

86. The apparatus according to claim 84 wherein the positron emitter generator comprises a cyclotron.

87. The apparatus according to claim 84 wherein the positron emitter is selected from the group consisting of $^{68}Ga$, $^{188}Re$, $^{11}C$, $^{13}N$, $^{18}F$, and $^{15}O$.

88. The apparatus according to claim 75 wherein the delivery unit comprises a fluid conduit having a first inlet operatively connected to the syringe.

89. The apparatus according to claim 88 wherein the fluid conduit further comprises a second inlet and a pressure syringe operatively connected to the second inlet.

90. The apparatus according to claim 88 wherein the fluid conduit further comprises an outlet for connecting the delivery unit to a balloon catheter.

91. An apparatus according to claim 75 comprising a syringe for receiving a solution comprising a radioactive material, the syringe comprising a plunger and a pressure sensor positioned within the syringe for measuring the pressure of fluid contained within the syringe.

92. The apparatus according to claim 91 wherein the pressure meter comprises a pressure transducer.

93. The apparatus according to claim 91 further comprising a locking mechanism movable between a locked position and an unlocked position, whereby the plunger is freely slidable within the syringe when the locking mechanism is in the unlocked position and the plunger is restrained by the locking mechanism when the locking mechanism is in the locked position.

94. The apparatus according to claim 93 wherein the locking mechanism comprises a central bore having internal threads and the plunger has a shaft comprising external threads, the external threads on the shaft of the plunger engaging the internal threads along the central bore of the locking mechanism thereby enabling the plunger to be longitudinally moved within the syringe by rotation of the plunger.

95. The apparatus according to claim 94 further comprising a sleeve of scintillating material positioned about the syringe for measuring a level of radiation associated with the radioactive material.

96. An apparatus for treating a body structure with a radioactive material comprising:
   a. a concentrator for receiving a first solution comprising a radioactive material and for producing a second solution comprising the radioactive material, the second solution having a greater concentration of the radioactive material than the first solution;
   b. a delivery unit operatively connected to the concentrator and adapted to transfer the second solution from the concentrator to a balloon; and
   c. a calibrator operatively associated with the concentrator for measuring a level of radiation associated with the radioactive material.

97. An apparatus for treating a body structure with a radioactive material comprising:
   a. a concentrator for receiving a first solution comprising a radioactive material and for producing a second solution comprising the radioactive material, the second solution having a greater concentration of the radioactive material than the first solution;
   b. a delivery unit operatively connected to the concentrator and adapted to transfer the second solution from the concentrator to a balloon; and
   c. a generator operatively connected to the concentrator for producing the first solution comprising the radioactive material.

98. An apparatus for treating a body structure with a radioactive material comprising:
   a. a concentrator for receiving a first solution comprising a radioactive material and for producing a second solution comprising the radioactive material, the concentrator comprising
      i. a cartridge having a hollow cavity, the cartridge comprising a first inlet for introducing the first solution into the cavity of the cartridge, and
      ii. a separating medium contained within the cavity of the cartridge for increasing the concentration of the radioactive material to provide the second solution; and
   b. a delivery unit operatively connected to the concentrator and adapted to transfer the second solution from the concentrator to a balloon.

99. An apparatus for treating a body structure with a radioactive material comprising:
   a. a concentrator for receiving a first solution comprising a radioactive material and for producing a second solution comprising the radioactive material, the volume of the second solution being less than the volume of the first solution, the concentrator comprising:
      i. a cartridge having a hollow cavity, the cartridge comprising a first inlet for introducing the first solution into the cavity of the cartridge;
      ii. a separating medium contained within the cavity of the cartridge for increasing the concentration of the radioactive material to provide the second solution;
   b. a delivery unit operatively connected to the concentrator and adapted to transfer the second solution from the concentrator to a balloon; and
   c. a generator operatively connected to the concentrator for producing the first solution comprising the radioactive material.

100. An apparatus for treating a body structure with a radioactive material comprising:
   a. a generator for receiving a first solution and for producing a second solution comprising a radioactive material;
   b. a receiving unit operatively connected to the generator for receiving the second solution from the generator, the receiving unit adapted to enable transfer of the second solution to a balloon; and
   c. a calibrator operatively associated with the receiving unit for measuring a level of radiation associated with the radioactive material.

* * * * *